US008835184B2

(12) United States Patent
Redmond et al.

(10) Patent No.: US 8,835,184 B2
(45) Date of Patent: Sep. 16, 2014

(54) ANALYSIS SYSTEM

(75) Inventors: Gareth Redmond, Ballinhassig (IE); Adrian Kewell, Douglas (IE); Jan Kruger, Cobh (IE); Georg Von Papen, Bad Hersfeld (DE)

(73) Assignee: Biosensia Patents Limited, Dublin (IE)

( * ) Notice: Subject to any disclaimer, the term of this patent is extended or adjusted under 35 U.S.C. 154(b) by 846 days.

(21) Appl. No.: 12/678,016

(22) PCT Filed: Sep. 15, 2008

(86) PCT No.: PCT/IE2008/000087
§ 371 (c)(1),
(2), (4) Date: Sep. 27, 2010

(87) PCT Pub. No.: WO2009/034563
PCT Pub. Date: Mar. 19, 2009

(65) Prior Publication Data
US 2011/0171754 A1 Jul. 14, 2011

Related U.S. Application Data

(60) Provisional application No. 60/960,069, filed on Sep. 14, 2007, provisional application No. 61/006,059, filed on Dec. 17, 2007.

(51) Int. Cl.
G01N 33/543 (2006.01)
G01N 21/05 (2006.01)
B01L 3/00 (2006.01)
G01N 21/03 (2006.01)

(52) U.S. Cl.
CPC .............. *G01N 21/05* (2013.01); *B01L 3/5025* (2013.01); *B01L 2300/0636* (2013.01); *B01L 2300/0627* (2013.01); *G01N 2021/054* (2013.01); *B01L 3/5029* (2013.01); *B01L 2300/0887* (2013.01); *B01L 2300/043* (2013.01); *B01L 2200/0642* (2013.01); *B01L 2300/0861* (2013.01); *G01N 2021/0346* (2013.01); *B01L 2300/0864* (2013.01); *B01L 3/502715* (2013.01); *B01L 2400/0406* (2013.01); *G01N 2021/058* (2013.01); *B01L 2200/027* (2013.01); *B01L 2200/025* (2013.01); *B01L 2300/069* (2013.01); *B01L 2200/16* (2013.01); *G01N 33/54386* (2013.01); *B01L 3/5023* (2013.01)
USPC ......................................................... 436/518

(58) Field of Classification Search
None
See application file for complete search history.

(56) References Cited

U.S. PATENT DOCUMENTS

| | | |
|---|---|---|
| 4,695,544 A | 9/1987 | Monaghan et al. |
| 4,703,017 A | 10/1987 | Campbell |
| 4,743,560 A | 5/1988 | Campbell et al. |
| 4,956,275 A | 9/1990 | Zuk et al. |
| 5,075,078 A | 12/1991 | Osikowicz et al. |
| 5,196,302 A | 3/1993 | Kidwell |
| 5,200,321 A | 4/1993 | Kidwell |
| 5,369,007 A | 11/1994 | Kidwell |
| 5,399,316 A | 3/1995 | Yamada |
| 5,468,648 A | 11/1995 | Chandler |
| 5,591,645 A | 1/1997 | Rosenstein |
| 5,602,040 A | 2/1997 | May |
| 5,622,871 A | 4/1997 | May |
| 5,656,503 A | 8/1997 | May |
| 5,872,713 A | 2/1999 | Douglas et al. |
| 5,874,216 A | 2/1999 | Mapes |
| 5,885,527 A | 3/1999 | Buechler |
| 5,922,615 A | 7/1999 | Nowakowski et al. |
| 6,019,944 A | 2/2000 | Buechler |
| 6,143,576 A | 11/2000 | Buechler |
| 6,156,270 A | 12/2000 | Buechler |
| 6,156,271 A | 12/2000 | May |
| 6,187,598 B1 | 2/2001 | May et al. |

(Continued)

FOREIGN PATENT DOCUMENTS

| | | |
|---|---|---|
| EP | 1046028 A1 | 10/2000 |
| EP | 1095270 A1 | 5/2001 |

(Continued)

OTHER PUBLICATIONS

International Search Report for PCT/IB2011/001473, mailed on Oct. 18, 2011 (5 pages).

(Continued)

*Primary Examiner* — Ann Lam
(74) *Attorney, Agent, or Firm* — Choate, Hall & Stewart LLP

(57) ABSTRACT

An analysis system comprises a sampling cartridge (11) comprising a housing (21, 22) having an inlet (23) for receiving a fluid sample, a sensor (26, 45), and a guide (40, 42) extending between the inlet and the sensor for guiding sample into contact with the sensor. The system also has an optical detection reader (13) for optically inspecting the sensor. The cartridge housing has an inspection window (34) and the reader (13) comprises a socket to receive the cartridge (11), and an optical system (1183, 1186) for inspecting the sensor through the window. The cartridge comprises parallel microfluidic channel (42) for flow of sample from the inlet into contact with the sensor. The sensor comprises discrete sensor pads (45) in at least one channel, with an antibody, an antigen, or molecular imprinted polymer. The channels are of microfluidic size, having a cross-sectional area in the range of about 0.3 mm$^2$ to about 5 mm$^2$. At least one channel comprises a reagent pad (43) upstream of the sensor (45). The inlet of the cartridge comprises an extraction chamber (23) communicating with a draining chamber having a top reservoir (61) and a bottom reservoir (63), in turn communicating with a distribution chamber (40). Together, these chambers and the interfaces between them guide sample flow in a uniform manner between the channels and also remove impurity particles and bubbles.

56 Claims, 30 Drawing Sheets

(56) References Cited

U.S. PATENT DOCUMENTS

| | | |
|---|---|---|
| 6,194,222 B1 | 2/2001 | Buechler et al. |
| 6,203,757 B1 * | 3/2001 | Lu et al. .................. 422/412 |
| 6,228,660 B1 | 5/2001 | May |
| 6,267,722 B1 | 7/2001 | Anderson et al. |
| 6,271,040 B1 | 8/2001 | Buechler |
| 6,297,020 B1 | 10/2001 | Brock |
| 6,297,060 B1 | 10/2001 | Nowakowski et al. |
| 6,319,665 B1 | 11/2001 | Zwanziger et al. |
| 6,319,676 B1 | 11/2001 | Nazareth et al. |
| 6,352,862 B1 | 3/2002 | Davis et al. |
| 6,368,478 B1 | 4/2002 | Huber et al. |
| 6,376,195 B1 | 4/2002 | Mapes |
| 6,399,398 B1 | 6/2002 | Cunningham et al. |
| 6,406,920 B1 | 6/2002 | Davis et al. |
| 6,440,309 B1 | 8/2002 | Cohen |
| 6,451,619 B1 | 9/2002 | Catt et al. |
| 6,454,726 B1 | 9/2002 | Catt et al. |
| 6,485,982 B1 | 11/2002 | Charlton |
| 6,551,495 B1 | 4/2003 | Porter et al. |
| 6,585,663 B1 | 7/2003 | Coley et al. |
| 6,596,140 B2 | 7/2003 | Nordman et al. |
| 6,602,719 B1 | 8/2003 | Carpenter |
| 6,632,655 B1 | 10/2003 | Mehta et al. |
| 6,663,831 B2 | 12/2003 | Konecke |
| 6,669,907 B1 | 12/2003 | Buechler |
| RE38,430 E | 2/2004 | Rosenstein |
| 6,737,278 B1 | 5/2004 | Carlsson et al. |
| 6,767,510 B1 | 7/2004 | Buechler |
| 6,767,714 B2 | 7/2004 | Nazareth et al. |
| 6,818,455 B2 | 11/2004 | May et al. |
| 6,830,731 B1 | 12/2004 | Buechler et al. |
| 6,844,200 B2 | 1/2005 | Brock |
| 6,877,892 B2 | 4/2005 | Karp |
| 6,905,882 B2 | 6/2005 | Buechler |
| 6,927,064 B1 | 8/2005 | Catt et al. |
| 6,951,631 B1 | 10/2005 | Catt et al. |
| 7,045,342 B2 | 5/2006 | Nazareth et al. |
| 7,090,802 B1 | 8/2006 | Wang et al. |
| 7,097,983 B2 | 8/2006 | Markovsky et al. |
| 7,109,042 B2 | 9/2006 | May et al. |
| 7,132,078 B2 | 11/2006 | Rawson et al. |
| 7,138,269 B2 | 11/2006 | Blankenstein |
| 7,141,212 B2 | 11/2006 | Catt et al. |
| 7,153,651 B1 | 12/2006 | Drewes et al. |
| 7,153,681 B1 | 12/2006 | Penfold et al. |
| RE39,644 E | 5/2007 | Alcorn et al. |
| RE39,664 E | 5/2007 | Gordon et al. |
| 7,238,537 B2 | 7/2007 | Davis et al. |
| 7,239,394 B2 | 7/2007 | Sharrock et al. |
| 7,244,392 B1 | 7/2007 | Konecke |
| 7,315,378 B2 | 1/2008 | Phelan et al. |
| 7,317,532 B2 | 1/2008 | Sharrock et al. |
| 7,384,796 B2 | 6/2008 | Davis et al. |
| 7,407,813 B2 | 8/2008 | Davis et al. |
| 7,410,768 B2 | 8/2008 | Butlin et al. |
| 7,416,700 B2 | 8/2008 | Buechler et al. |
| 7,445,941 B2 | 11/2008 | Buechler |
| 7,459,314 B2 | 12/2008 | Guo et al. |
| 7,524,456 B1 | 4/2009 | Buechler |
| 7,611,669 B1 | 11/2009 | Crisanti et al. |
| 7,615,191 B2 | 11/2009 | Buechler |
| 7,632,460 B2 | 12/2009 | Catt |
| 2002/0052049 A1 * | 5/2002 | Weigl et al. .................. 436/180 |
| 2002/0150501 A1 | 10/2002 | Robertson et al. |
| 2003/0119203 A1 | 6/2003 | Wei et al. |
| 2004/0023412 A1 | 2/2004 | Carlsson |
| 2004/0048322 A1 * | 3/2004 | Nakajima .................. 435/7.92 |
| 2004/0077103 A1 | 4/2004 | Buechler |
| 2004/0106162 A1 * | 6/2004 | Glasel et al. .................. 435/7.32 |
| 2004/0142495 A1 | 7/2004 | Hartman et al. |
| 2004/0161859 A1 | 8/2004 | Guo et al. |
| 2004/0228764 A1 | 11/2004 | Stephens et al. |
| 2004/0241047 A1 | 12/2004 | Buechler |
| 2005/0079634 A1 | 4/2005 | Wilding et al. |
| 2005/0106739 A1 * | 5/2005 | Cabuz et al. .................. 436/63 |
| 2005/0130292 A1 | 6/2005 | Ahn et al. |
| 2006/0018790 A1 * | 1/2006 | Naka et al. .................. 422/58 |
| 2006/0029924 A1 | 2/2006 | Brewster et al. |
| 2006/0040408 A1 | 2/2006 | Jones et al. |
| 2006/0276108 A1 * | 12/2006 | Benson .................. 451/41 |
| 2007/0219908 A1 | 9/2007 | Martinez |
| 2008/0038759 A1 | 2/2008 | Keren et al. |
| 2009/0101559 A1 * | 4/2009 | Bala Subramaniam et al. .................. 210/194 |
| 2009/0162833 A1 | 6/2009 | Mertens et al. |
| 2009/0196792 A1 | 8/2009 | Raj et al. |
| 2010/0081216 A1 * | 4/2010 | Yager et al. .................. 436/524 |
| 2010/0151553 A1 * | 6/2010 | Bjork et al. .................. 435/173.7 |
| 2012/0245038 A1 * | 9/2012 | Linton et al. .................. 506/2 |

FOREIGN PATENT DOCUMENTS

| | | |
|---|---|---|
| EP | 1175940 A1 | 1/2002 |
| EP | 1 387 170 A1 | 2/2004 |
| EP | 1792655 A1 | 6/2007 |
| EP | 2049897 A1 | 4/2009 |
| GB | 2432420 A | 5/2007 |
| WO | WO-9935486 A1 | 7/1999 |
| WO | WO-0004381 | 1/2000 |
| WO | WO-2004038414 A1 | 5/2004 |
| WO | WO-2004087322 A2 | 10/2004 |
| WO | WO 2006/083053 A1 | 8/2006 |
| WO | WO-2007019479 A2 | 2/2007 |
| WO | WO-2007065695 A1 | 6/2007 |
| WO | WO-2008018073 A1 | 2/2008 |
| WO | WO-2008070865 A2 | 6/2008 |
| WO | WO-2008128534 A1 | 10/2008 |

OTHER PUBLICATIONS

Written Opinion for PCT/IB2011/001473, mailed on Oct. 18, 2011 (6 pages).
International Search Report for PCT/IE2008/000087 dated Mar. 20, 2009.
Written Opinion for PCT/IE2008/000087 dated Mar. 14, 2010.

* cited by examiner

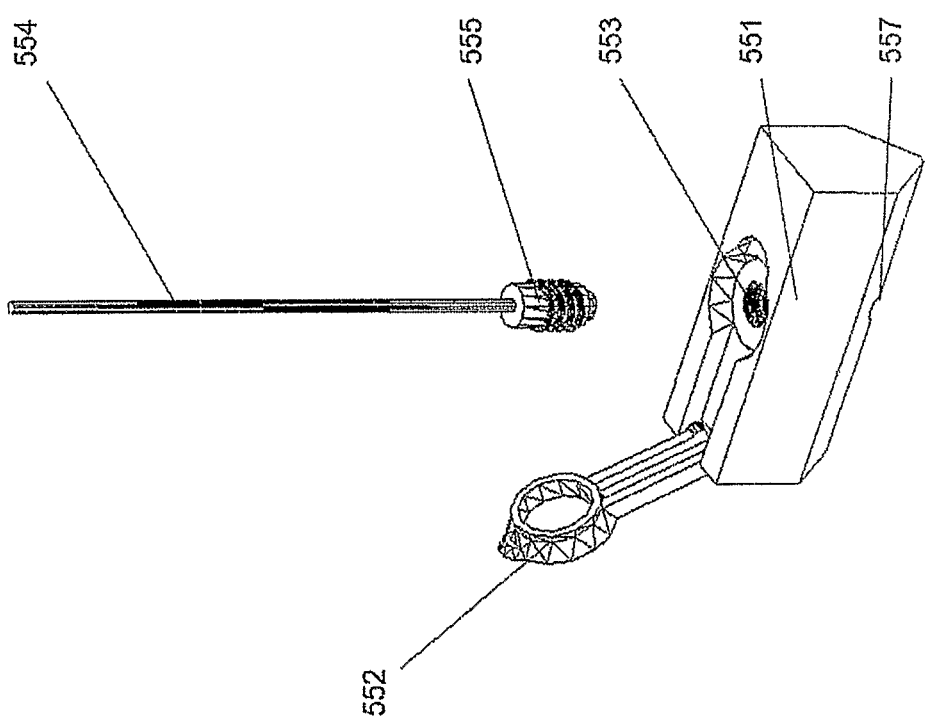

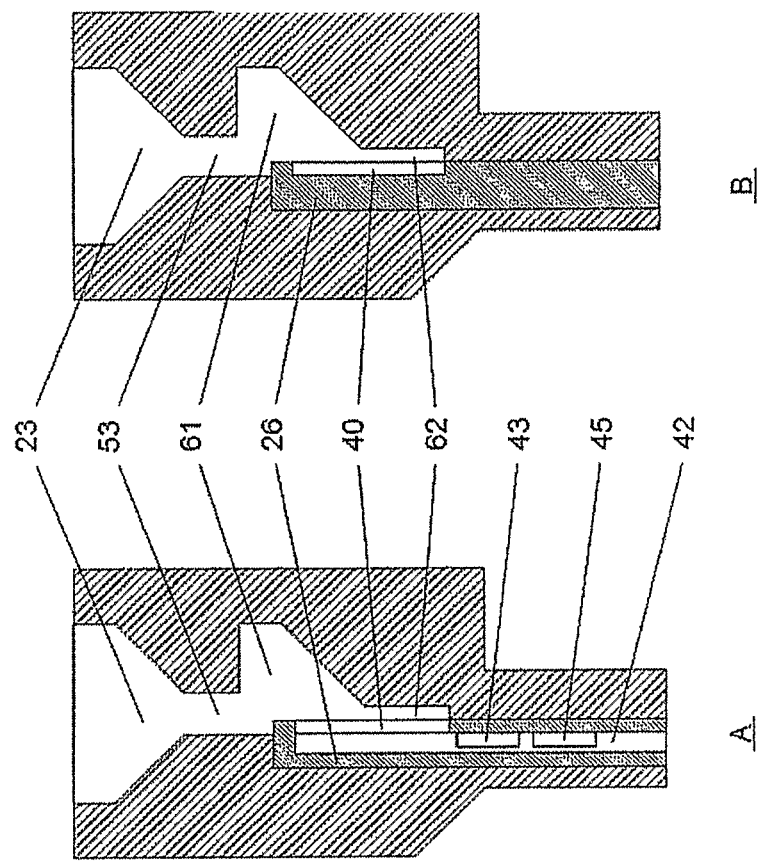
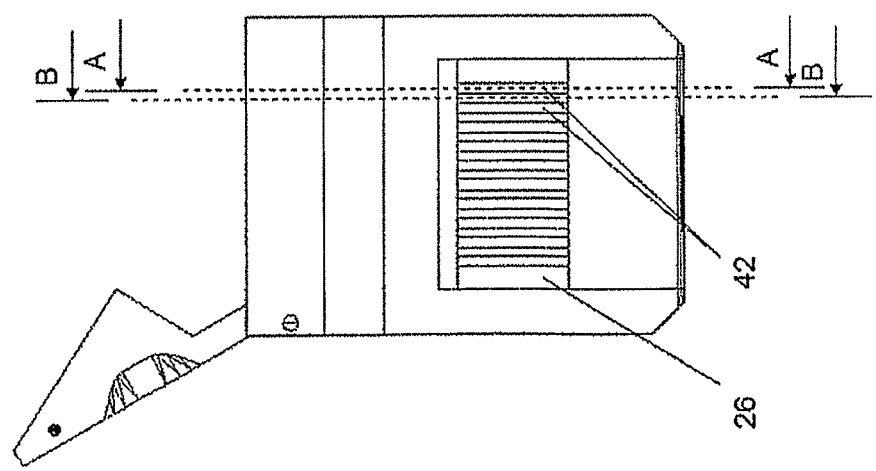
Figure 6a

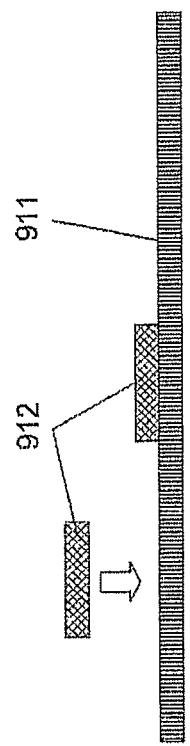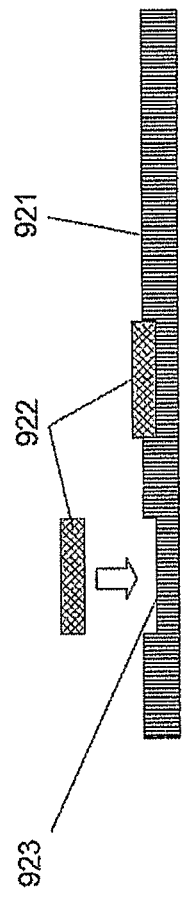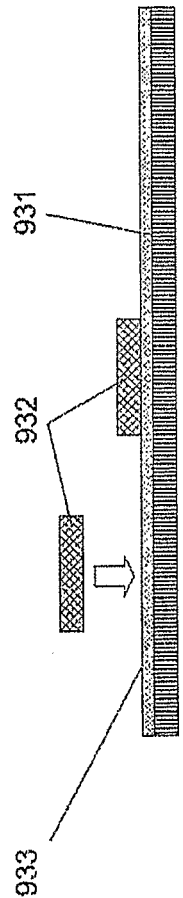

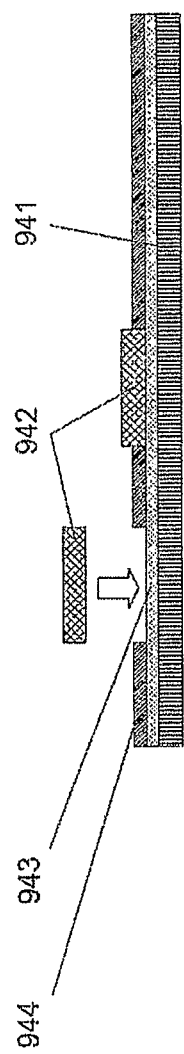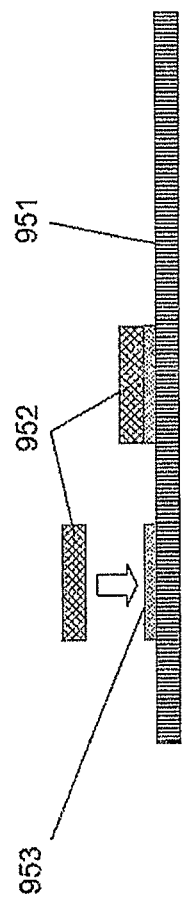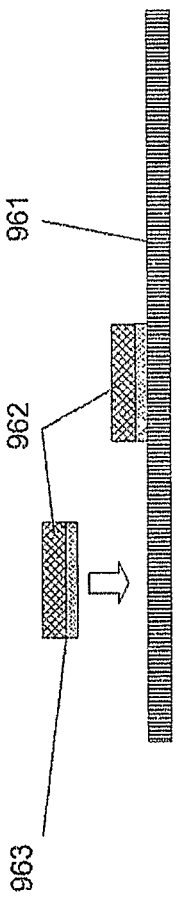

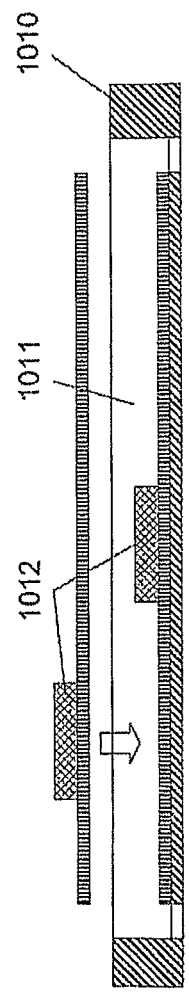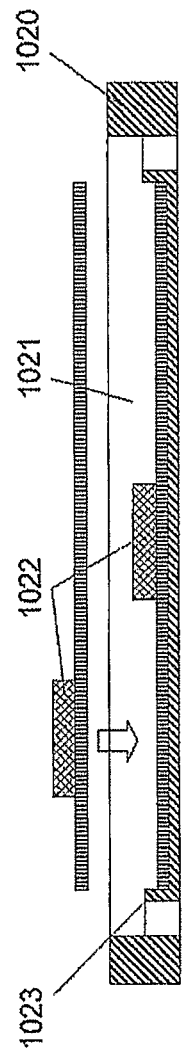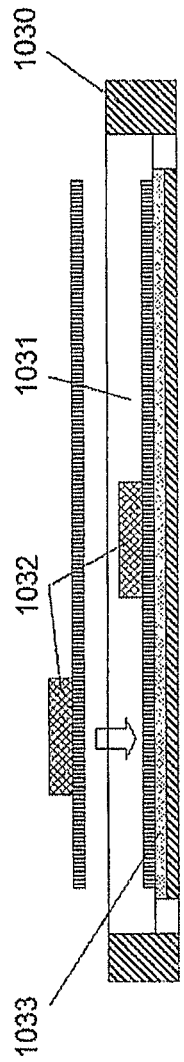

ANALYSIS SYSTEM

INTRODUCTION

The present invention relates to analyses of fluid samples to detect the presence of target analytes.

WO2006017175 describes an apparatus for drugs of abuse screening, including a lateral flow immunoassay, and two types of test are carried out in the one housing.

The invention is directed towards providing improved screening in terms of consistency and repeatability of results, and/or extent of multiplexing of different tests, and/or ability to cater for impurities in sample fluids.

STATEMENTS OF INVENTION

According to the invention, there is provided an analysis system comprising:
- a sampling cartridge comprising a housing having an inlet for receiving a fluid sample, a sensor, and a guide extending between the inlet and the sensor for guiding sample into contact with the sensor; and
- an optical detection reader for optically inspecting the sensor;
- wherein the cartridge housing comprises an inspection window; and the reader comprises a socket to receive at least part of the cartridge, and an optical system for inspecting the sensor through the window, and
- wherein the cartridge guide comprises at least one microfluidic channel for flow of sample from the inlet into contact with the sensor.

In one embodiment, the cartridge guide comprises a plurality of channels, and the channels are preferably separate, without possibility of sample cross-over. The sensor may comprise discrete sensor elements in the at least one channel, and it may include an antibody, an antigen, or molecular imprinted polymer on a substrate.

Preferably, each channel has a cross-sectional area in the range of about 0.3 $mm^2$ to about 5 $mm^2$, and most preferably in the range of about 1 $mm^2$ to about 2 $mm^2$. In one embodiment, at least one channel comprises a reagent pad upstream of the sensor, and preferably at least one channel has a free space diffusion zone between the reagent pad and the sensor, the free space being sufficient for comprehensive dissolution of reagent into the sample fluid before reaching the sensor.

In one embodiment, at least one channel comprises an absorbent pad downstream of the sensor, and preferably at least one channel has an opening at the end of the channel to act as a vent to assist sample fluid flow, and preferably at least one channel has a free space diffusion zone between the sensor and the absorbent pad. In one embodiment, the sensor and each pad are on a strip adhered to a base of the at least one channel.

In one embodiment, there is a gap above the sensor in the channel, the gap being wide enough to permit flow above the sensor of a small quantity of sample fluid, sufficient to contribute to capillary flow along the channel, and preferably the gap is in the range of 0.05 mm and 0.5 mm.

In one embodiment, the inlet comprises a swab pressing means. Preferably, the pressing means comprises a hinged handle, wherein the handle forms a cover or lid for the housing, closure of the handle causing an inserted swab to be pressed. In one embodiment, the inlet has an opening configured to receive a swab and allow manual pressing of the swab head. In one embodiment, the inlet comprises a membrane over an inlet volume to allow injection of sample by a syringe. In one embodiment, the inlet comprises an extraction chamber in fluid communication with a draining chamber, fluid travelling from the extraction chamber to the draining chamber in a first direction, and the draining chamber is in fluid communication with at least one channel.

In one embodiment, the draining chamber comprises a top reservoir and a bottom reservoir, the fluid flowing from the top reservoir into the bottom reservoir in the first direction; and an interface between the top and the bottom reservoir configured to direct the flow of the fluid along the first direction. In one embodiment, the top and the bottom reservoirs have a substantially similar width in a second direction perpendicular to the first direction, and the bottom reservoir has a width in a third direction perpendicular to the first direction and the second direction, and the top reservoir has a width in the third direction larger than that of the bottom reservoir; and the interface between the top and the bottom reservoirs is configured to direct the flow of the fluid along the first direction and the second direction inside the bottom reservoir.

In one embodiment, there is a plurality of channels and the cartridge comprises a distribution chamber configured for spreading sample fluid flow from the bottom reservoir in the second direction and in the third direction into the channels. Preferably, the interface between the top reservoir and the bottom reservoir is configured to separate or eliminate a bubble in sample fluid above the interface from sample fluid flowing in the first direction across the interface into the bottom reservoir. In one embodiment, the top reservoir has a large volume to assist bubble removal. In one embodiment, there is a narrow interface between the extraction chamber and the top reservoir, thus blocking impurity particles. In one embodiment, the interface is in the form of an elongate slot extending in said second direction. In one embodiment, an intersection of the distribution chamber and the channels is configured with dimensions and shape determining the size of impurity particles blocked from passing from the distribution chamber to the channels.

In one embodiment, the bottom reservoir and the distribution chamber each have a small dimension in the third direction, said dimension being in the range of 0.25 mm to 2.0 mm.

In one embodiment, a reagent pad located in at least one channel upstream of the sensor has a porosity determining the size of impurity particles withheld from moving towards the sensor in addition to being optimised for conjugate release.

In one embodiment, the at least one channel is in a substrate sandwiched between cartridge housing parts. In one embodiment, the cartridge housing has placement features corresponding to and engaging placement features on the substrate, in order to facilitate positioning of said substrate with respect to the inlet. In one embodiment, the substrate has alignment features protruding outside of the cartridge housing and being configured for engagement with corresponding engagement features of the optical detection reader, thereby providing registration between the sensor and the optical detection reader. Preferably, an optical detection reader alignment feature comprises a biased latch member configured for retaining the substrate in position despite mechanical shock. In one embodiment, the cartridge housing has guiding rails that facilitate its insertion into the optical detection reader.

In another aspect, the invention provides a microfluidic structure for flow control and delivery of a fluid to an analyzing area, comprising:
- an extraction chamber in fluid communication with a draining chamber, fluid travelling from the extraction chamber to the draining chamber in a first direction; the draining chamber comprising a top reservoir and a bottom reservoir, the top and the bottom reservoirs having a substantially similar width in a second direction perpendicular to the first direction, and the bottom reservoir having a width in a third direction perpendicular to the first direction and the second direction, and the top reservoir having a width in the third direction larger than that of the bottom reservoir, the fluid flowing from the top reservoir into the bottom reservoir in the first direction;

an interface between the top and the bottom reservoir configured to redirect the flow of the fluid along the first direction and the second direction inside the bottom reservoir;

a distribution chamber, comprising a plurality of inlet channels connected with the bottom reservoir, the fluid flowing from the bottom reservoir into the plurality of inlet channels each inlet channel comprising an analyzing area connected with the bottom reservoir, splitting the fluid into a plurality of inlet channels; and a porous absorbing material, spaced apart from the analyzing area by a non-porous portion of the channel, and configured to extract fluid from the fluid analyzing area.

In another aspect, the invention provides a method for flow control and delivery of a fluid via a microfluidic structure to an analyzing area, the method comprising:

extracting a fluid in the first direction from an extraction chamber to a top reservoir of a draining chamber;

directing the fluid from the top reservoir to a bottom reservoir of the draining chamber, the top and the bottom reservoirs having a substantially similar width in a second direction perpendicular to the first direction, and the bottom reservoir having a width in a third direction perpendicular to the first direction and the second direction, and the top reservoir having a width in the third direction larger than the width of the bottom reservoir, the fluid flowing from the top reservoir into the bottom reservoir in the first direction;

redirecting, by an interface between the top and the bottom reservoir, the flow of the fluid from the top reservoir to bottom reservoir such that fluid flows in the first direction and the second direction inside the bottom reservoir;

splitting, by a distribution chamber comprising a plurality of inlet channels each inlet channel comprising an analyzing area connected with the bottom reservoir, the fluid flowing from the bottom reservoir into the plurality of inlet channels; and extracting, by a porous absorbing material spaced apart from the analyzing area by a non-porous portion of the channel, fluid from the fluid analyzing area.

In another aspect, the invention provides a microfluidic structure for separating bubbles from a fluid, comprising:

an extraction chamber in fluid communication with a draining chamber, fluid travelling from the extraction chamber to the draining chamber in the first direction; the draining chamber comprising a top reservoir and a bottom reservoir, the top and the bottom reservoirs having a substantially similar width in a second direction perpendicular to the first direction, and the bottom reservoir having a width in a third direction perpendicular to the first direction and the second direction, and the top reservoir having a width in the third direction larger than that of the bottom reservoir, the fluid flowing from the top reservoir into the bottom reservoir in the first direction; an interface between the top reservoir and the bottom reservoir, substantially perpendicular to the interface between the top reservoir and the bottom reservoir, wherein the interface is configured to separate a bubble above the interface from the fluid flowing in the first direction across the interface into the bottom reservoir.

In another aspect, the invention provides a method for separating bubbles from a fluid in a microfluidic structure, the method comprising:

extracting a fluid in a first direction from an extraction chamber to a top reservoir of a draining chamber;

directing the fluid from the top reservoir to a bottom reservoir of the draining chamber, the top and the bottom reservoirs having a substantially similar width in a second direction perpendicular to the first direction, and the bottom reservoir having a width in a third direction perpendicular to the first direction and the second direction, and the top reservoir having a width in the third direction larger than the width of the bottom reservoir, the fluid flowing from the top reservoir into the bottom reservoir in the first direction;

separating a bubble from the fluid using an interface between the top reservoir and the bottom reservoir, wherein in response to the flow from the top reservoir into the bottom reservoir in the first direction substantially perpendicular to the interface between the top reservoir and the bottom reservoir, a bubble above the interface is separated from the fluid flowing in the first direction across the interface into the bottom reservoir.

In another aspect, the invention provides a microfluidic structure for flow control of a fluid, comprising:

a fluidic channel, configured to guide a flow of a fluid comprising a drug in a first direction, the fluidic channel having a width in a second direction perpendicular to the first direction and a depth in a third direction perpendicular to the first direction and the second direction, the fluidic channel comprising a non-porous material and three non-concatenated channel portions segregated along the first direction by a reagent pad followed by a sensor pad in respect to the first direction, the sensor pad separated from the reagent pad by a channel portion, and having an absorption pad interfacing with a channel portion following the reagent pad, the sensor pad and the two channel portions along the first direction and not interfaced with the reagent pad or the sensor pad, the absorption pad comprising a fluid absorbing material;

the reagent pad, having a size in the second direction substantially similar to the width of the fluidic channel and having a size in the third direction substantially similar to the depth of the fluidic channel, and comprising a conjugate of a drug and label, wherein the conjugate is soluble in an oral fluid;

the sensor pad, having a size in the second direction substantially similar to the width of the fluidic channel and having a size in the third direction substantially similar to the depth of the fluidic channel, comprising a molecularly imprinted polymer or an antigen or antibodies which bind the drug and the conjugate.

In another aspect, the invention provides a method for flow control of a fluid, comprising:

guiding, by a structure a flow of a fluid comprising a drug, the structure comprising a fluidic channel having a width in a second direction perpendicular to the first direction and a depth in a third direction perpendicular to the first direction and the second direction, the fluidic channel comprising a non-porous material and three non-concatenated channel portions segregated along the first direction by a reagent pad followed by a sensor pad in respect to the first direction, the sensor pad separated from the reagent pad by a channel portion, and having a absorption pad interfacing with a channel portion following the reagent pad, the sensor pad and the two channel portions along the first direction and not interfaced with the reagent pad or the sensor pad, the absorption pad comprising a fluid absorbing material;

releasing a conjugate of a drug and label from the reagent pad into the fluid as a result of the reagent pad having a size in the second direction substantially similar to the width of the fluidic channel and having a size in the third direction substantially similar to the depth of the fluidic channel and the reagent pad comprising a conjugate which is soluble in the fluid; and bonding drug and conjugate from the fluid to the sensor pad as a result of the sensor pad having a size in the second direction substantially similar to the width of the fluidic channel and having a size in the third direction substantially similar to the depth of the fluidic channel and the sensor pad comprising a molecularly imprinted polymer, an antigen or an antibody which binds the drug and the conjugate.

DETAILED DESCRIPTION OF THE INVENTION

Brief Description of the Drawings

The invention will be more clearly understood from the following description of some embodiments thereof, given by way of example only with reference to the accompanying drawings in which:

FIGS. 5b to 5h are views of alternative arrangements for receiving swabs or other sample collection devices;

FIG. 6a shows the cartridge of FIG. 2 in more detail.

FIGS. 9a to 9g are diagrams showing other fluidic chip arrangements, differing in terms of how pads are inserted in the channels;

FIGS. 10a to 10f are diagrams showing further fluidic chip arrangements, in which pads are pre-mounted on strips which are then inserted in the channels;

DESCRIPTION OF THE EMBODIMENTS

Figure 1:
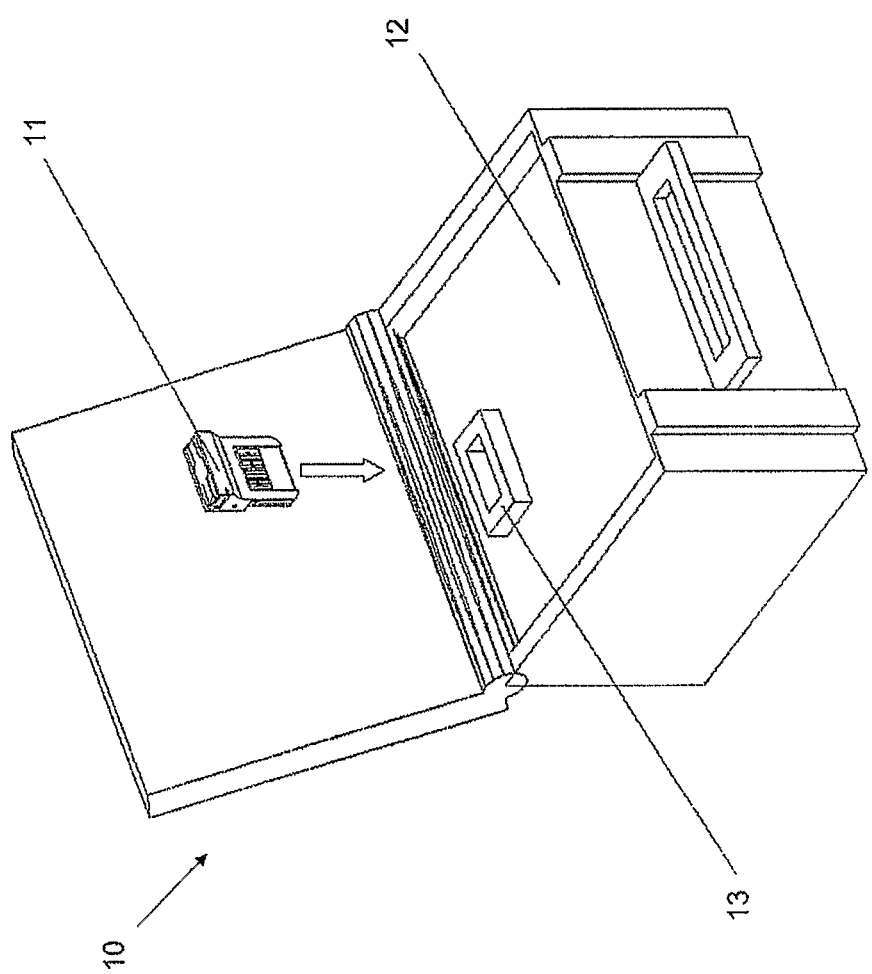
FIG. 1 is a perspective view of an analysis system, showing how it is carried and used at a general level in one embodiment.

In one aspect, an analysis system of the present invention comprises a sampling cartridge for receiving a fluid sample. In some embodiments the cartridge is adapted for receiving a swab, and for retrieving and transferring a swabbed sample of fluid, such as oral fluid, to active sensors in one or more channels. The channels may have microfluidic dimensions, for fast sampling and small sample volumes for applications such as screening for drugs of abuse. In various embodiments, each channel has a reagent pad and a sensor pad, and in various embodiments the sensor may be of the antibody, and/or antigen, and/or molecularly imprinted polymer (MIP) type. Once the sample has been inserted into the cartridge, the cartridge is inserted into an optical detection reader for sample analysis. Because there are multiple parallel channels, there is a large extent of analysis multiplexing possible, there being one analysis per channel.

It is to be understood that a variety of fluid sample types at the microfluidic volume level can be analyzed by various embodiments of the analysis systems such as for example, physiological fluid samples, food, beverages, and environmental samples. Examples of physiological fluids, include, but are not limited to, blood, serum, plasma, sweat, tears, urine, peritoneal fluid, lymph, vaginal secretion, semen, spinal fluid, ascetic fluid, saliva, sputum, breast exudates, and combinations thereof. Examples of analytes that can be detected in physiologicall fluids include, but are not restricted to, proteins, (including immunoglobulins, hormones etc.), polynucleotides, steroids, drugs and infectious disease agents (of bacterial or viral origin, eg. Influenza, Streptococcus and Chlamydia) or antibodies to infectious disease agents (eg. HIV, Rubella and Hepatitis). Examples of foods or beverages include, but are not limited to, wine, honey, soy sauce, poultry, pork, beef, fish, shellfish, and combinations thereof. Examples of environmental samples include, but are not limited to, water, environmental effluent, environmental leachates, waste water, pesticides, insecticides, waste by products, and combinations thereof.

As used herein, the term "oral fluid" describes any fluid collected from the oral cavity, e.g., by use of absorbents, or expectoration or direct collection of glandular secretions from the salivary glands. It will be appreciated that oral fluids are often complex mixtures of different secretions including glandular secretions and oral mucosal transudate. These generally contain varying concentrations of proteins (eg. enzymes) bacteria, amino-acids, glucose, and a variety of inorganic ions, epithelial cells, leucocytes, food residue, and various dissolved gases. The documented viscosity found in human saliva ranges from approximately 2.8 centipoise (cp) to approximately 15.5 cp. In various embodiments, use of certain drugs of abuse may cause "dry mouth" among certain individuals, and the saliva of these drug users may be more viscous than normal. In certain embodiments the fluid sample sizes may be at the microfluidic level, meaning in the range of a few microliters up to tens of milliliters.

As used herein, term "molecularly imprinted polymer" or "MIP" denotes selective binding materials prepared by polymerization of one or more functional monomers and one or more cross-linkers in the presence of a template molecule. Extraction of the template gives rise to selective recognition sites. These are complementary in functionality and spatial features of the template by virtue of the fixation of pre-polymerisation complexes present in the polymerisation mixture by the formation of a highly cross-linked porous matrix. The resulting molecularly imprinted polymer is capable of rebinding the template molecule selectively under appropriate conditions. MIPs may be prepared by a number of polymerisation techniques and the interactions between the template and polymer may be covalent, semi-covalent or non-covalent in nature, or any combination of the above. For a more detailed introduction to MIPs, refer to "Mimicking molecular receptors for antibiotics—analytical implications" by Fernandez-Gonzalez, A.; Guardia, L.; Baadia-Laino, R.; Diaz-Garcia, M. E. *Trends Anal. Chem.* 2006, 25, 949-957.

Referring to FIG. 1, in one aspect an analysis system 10 comprises a disposable cartridge 11 and an integrated optical detection reader 13. In various embodiments, the reader 13 may be integrated with an apparatus 12 comprising a mother instrument for transport and ease of handling. In various embodiments the cartridge 11 is designed for the retrieval of a fluid sample from a fluid sample collection device, the conditioning of that fluid sample to reduce contaminations such as bubbles and solid impurities, and for subsequently facilitating single or multiple analyses of the conditioned sample to ascertain the presence and concentrations of specific target analytes or groups of target analytes. According to some of these embodiments the optical detection reader 13 receives and aligns the cartridge 11, to substantially simultaneously interrogate the status of each of the individual analyses taking place within the cartridge 11, and to subsequently process and display the obtained signals.

Figure 2:
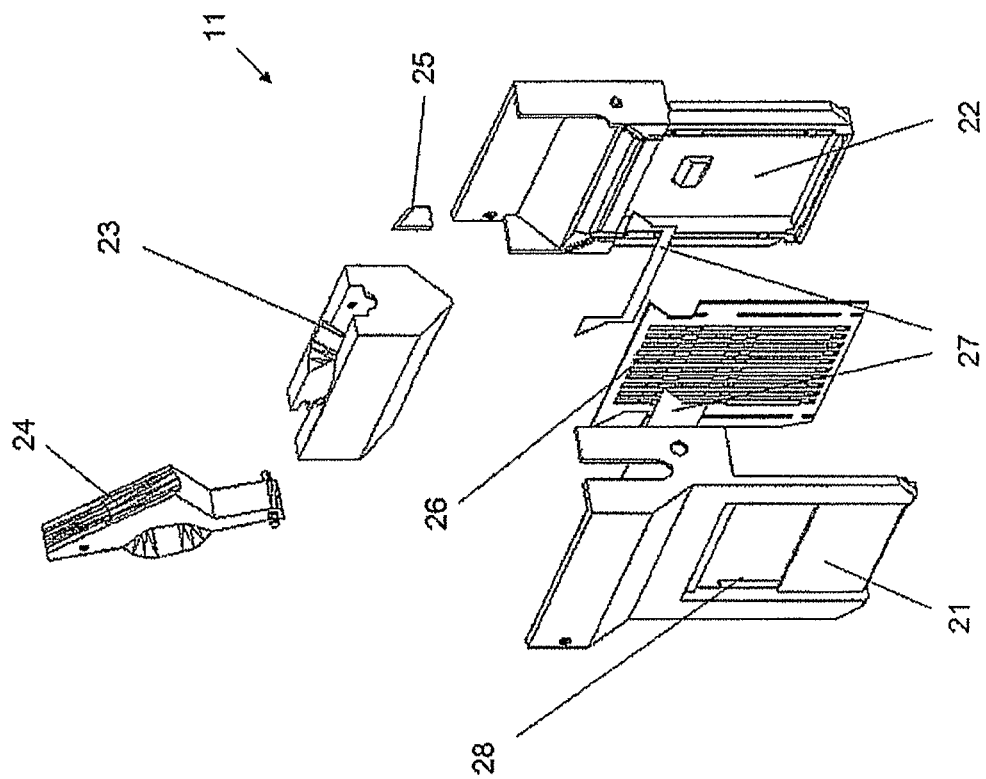
FIG. 2 is an exploded view showing individual components of a sampling cartridge of the analysis system.

Referring to FIG. 2, in various embodiments the cartridge 11 comprises a front part 21, a rear part 22, and an extraction chamber 23 with a hinged lid 24, a guillotine 25, a fluidic chip 26 and water tight seals 27. In various embodiments, the seals 27 may be made of Silicone material. Alternatively the seals may be made of thermoplastic elastomers (TPE) and can be integrated into the housing by means of two shot injection moulding. Alternatively the features of the extraction chamber 23 can be incorporated into the front part 21 and the rear part 22.

Figure 3:
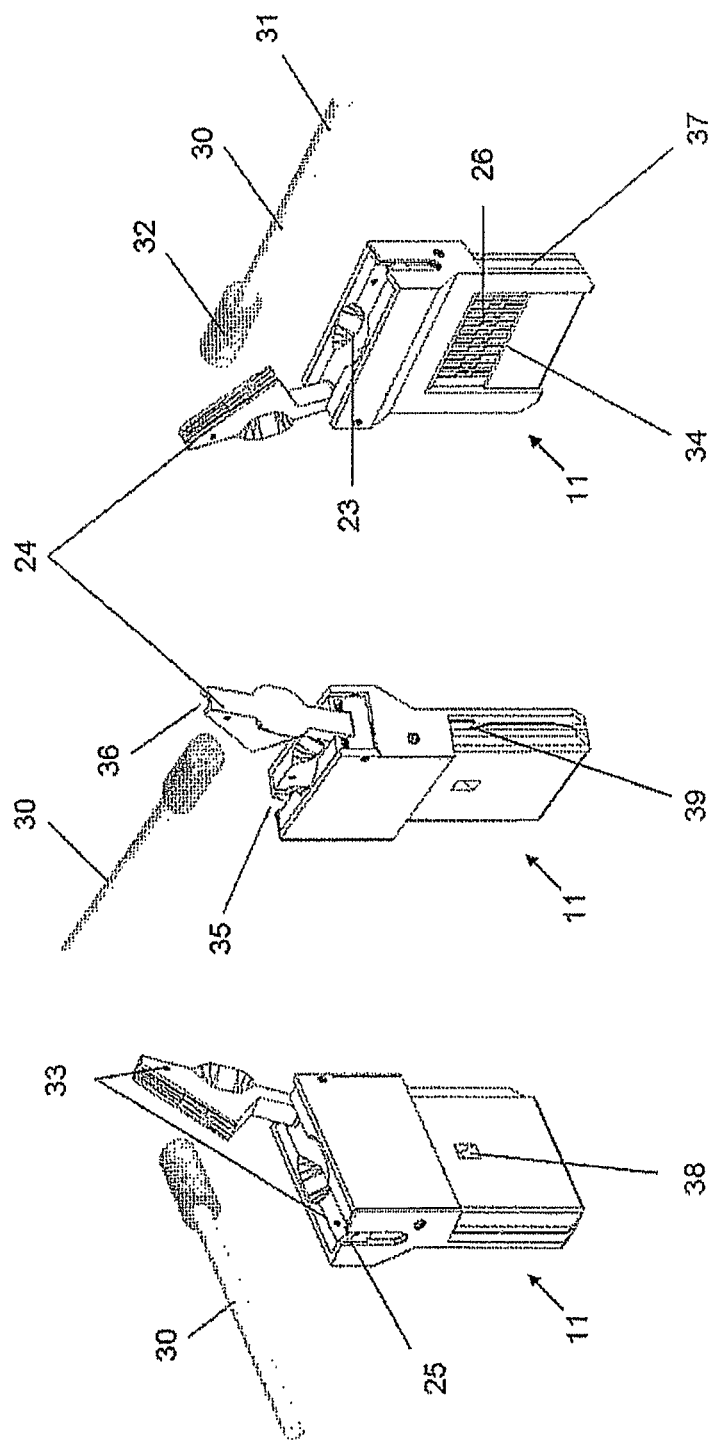
FIG. 3 is a set of three perspective views of the cartridge.

Referring to FIG. 3, in various embodiments the cartridge 11 may be designed to work in conjunction with a swab 30 comprising a handle 31 and a foam head 32 that permits absorption of a sample of swabbed fluid from a donor's mouth. Upon insertion of a swab 30 into the extraction chamber 23, the chamber is closed by pushing down the hinged lid 24 until optional locking features 33 passively lock the lid in place. The housing end wall and the lid 24 have a co-operating recess 35 and notch 36, respectively, that allow the swab handle 31 to protrude from the cartridge while the swab head 32 is retained, enclosed in the extraction chamber 23. In various embodiments, during the closing process, a guillotine blade 25 may be employed to ensure that no part of the swab 30 protrudes outside of the extraction chamber 23. In this way, the swab head 32 may be kept, without risk of cross-contamination, permitting further analysis of the retained fluid sample in a laboratory at a later time. When the lid 24 is closed upon a swab 30, the fluid sample is retrieved from the swab 30 as the lid 24 compresses the sponge attached to the swab head 32. The fluid sample is forced to run into an internal fluidic network that is located above a fluidic chip 26, the active sensor locations which are visible through an optical inspection window 34. During this step, the fluid sample may be passively conditioned to reduce contaminations such as bubbles and solid impurities. When the conditioned fluid sample flows onwards into the fluidic chip 26 and eventually passes near individual active sensors inside the chip, an assay occurs at each sensor producing a signal that can be read, for example, by eye and/or by an optical transducer such as the reader 13, through the inspection window 34. In order to ensure that accurate optical measurements may be carried out at each active sensor location using the reader 13, the cartridge 11 is equipped with guiding 37, locking 38 and alignment 39 features that facilitate providing reproducible and robust registration with the internal mechanics of the optical detection reader 13 by direct engagement.

Figure 4A:
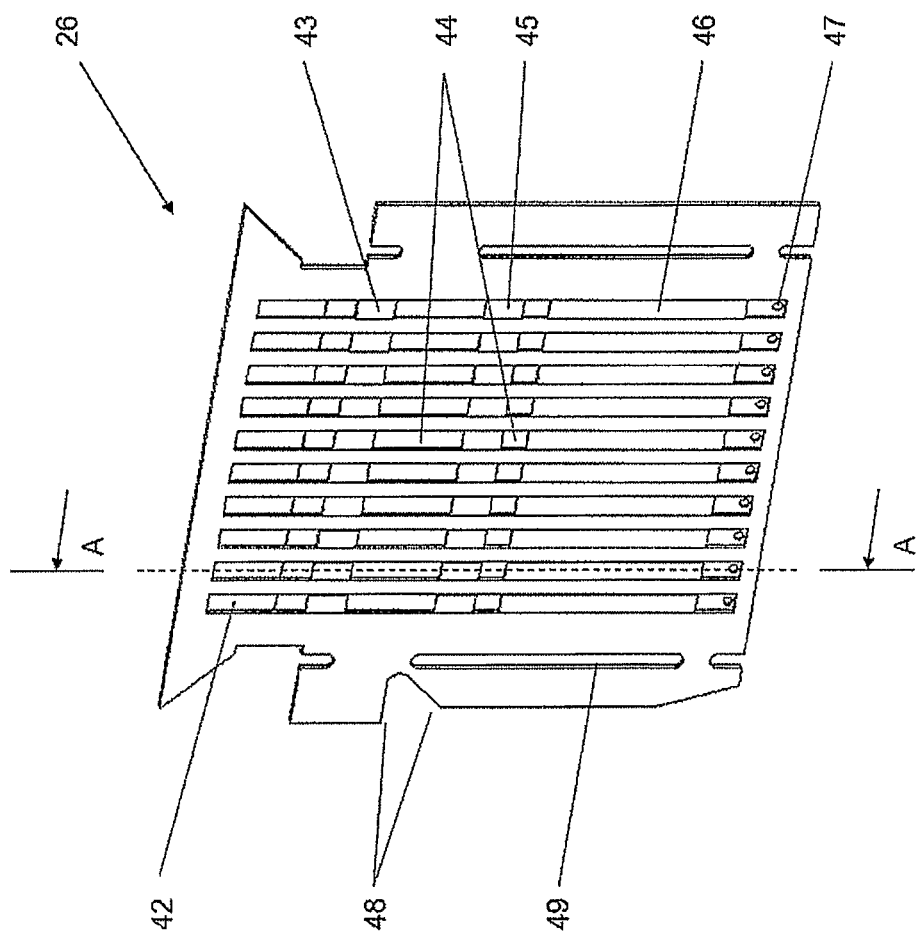
FIGS. 4a and 4b are front and rear views of a fluidic chip of the cartridge, the fluidic chip having a substrate with channels for guiding sample fluid into the sensor.
Figure 4B:
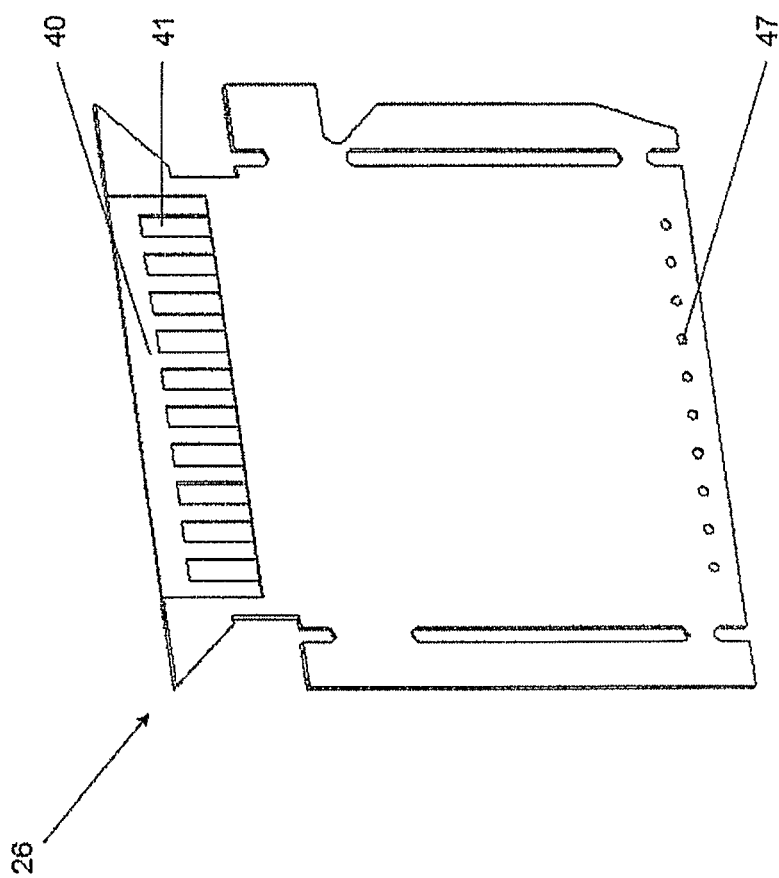

Referring to FIGS. 4a and 4b, the fluidic chip 26 may be configured to permit multiple, substantially simultaneous, rapid assays to be performed with each assay resulting in production, at each active sensor location, of a signal that can be read, for example, by the optical transducer. In one embodiment, the fluidic chip 26 may comprises multiple fluidic channels 42, with dimensions of 1.7 mm in width, 0.55 mm in depth and 35 mm in length, spaced 3 mm apart and linked together via a distribution chamber 40. More generally, the dimensions may be in the range of about 1.3 to about 5 mm in width, about 0.25 mm to about 1 mm in depth and about 25 mm to 50 mm in length, spaced, between 0.5 to 5 mm apart. The resulting cross-sectional area of each channel can be defined to be in the range of about 0.3 $mm^2$ to about 5 $mm^2$, preferably 1 $mm^2$ to 2 $mm^2$.

In various embodiments, each channel may comprise a sample inlet port 41, a reagent pad 43, a diffusion zone 44, a sensor pad 45, a second diffusion zone 44, an absorbent pad 46, a channel vent 47, and, if necessary, a surfactant or hydrophilic coating on the internal channel surfaces. In various embodiments, the chip 26 may consist of a laminated PET substructure and PMMA superstructure. Alternatively such fluidic chips may be fabricated inexpensively with micro- to milli-meter dimensions in materials such as polymers and plastics, e.g. Cyclic Olefin Copolymers (COC), Polyethylene terephthalates (PET) or Polypropylene (PP) using, for example, injection moulding, screen printing, hot embossing, laser cutting, die cutting, and in silicon and other materials using micro-fabrication techniques such as photolithography and etching.

It will be appreciated that a variety of designs can be used ranging from complex microfluidic lab-on-a-chip designs in which the elements of an analytical instrument are reproduced on a silicon wafer or some other chip, to simpler designs in which external forces such as gravity or wetting processes such as capillary action or other fluidic effects are used to move reactants through microscale, or larger, channels in the fluidic chip. The structure of the flow path, as shown from top to bottom in FIGS. 4a and 4b, will generally be designed to effectively convey the fluid sample through the fluidic chip 26: In various embodiments, the sample inlet ports 41 will be generally dimensioned to permit efficient introduction of the fluid sample into the one or more fluidic channels 42 which subsequently flows across the pads 43, 45 and 46, and down to the channel vents 47 where fluid flow eventually terminates. In such embodiments, the fluid sample flow characteristics may be regulated by appropriate setting of the relative dimensions, porosity and surface chemistry of each of the pads 43, 45 and 46, of the channels 42 and of the channel vents 47.

The fluid sample moving along a channel 42 first comes into contact with a reagent pad 43. The reagent pad 43 is located upstream of the sensor pad 45, separated by a diffusion zone 44. The reagent pad 43 contains a specific quantity of dried target-linker-label conjugates, which has been specifically synthesised for the target analyte, along with quantities of other substances necessary to facilitate the assay. When more than one channel is used to detect different analytes, each reagent pad may contain a conjugate which has been specifically synthesised for each target analyte. In certain embodiments, the flourescent labels may be functionalised derivatives of the Alexa Fluor (e.g. AlexaFluor 647), BODIPY, Dylight Fluor (e.g. Dylight 649), Cascade Blue, Oregon Green, Lucifer Yellow and Texas Red series of commercially available dyes, or other fluorescent dyes including, but not restricted to, coumarin, flourescein, rhodamine, eosin, erythrosine and other visible-emitting dyes. It will be appreciated that any of a wide variety of fluorescence conjugation techniques could be used as understood by those skilled in the art.

In various embodiments, when the fluid sample moving along a channel 42 comes into contact with a reagent pad 43, the fluid flows about each pad thereby facilitating the rapid dissolution of conjugates and other substances necessary to facilitate the assay into the fluid (eg. in less than 3 sec). The fluid then flows along the section of the channel 42 referred to as the diffusion zone 44, subsequently presenting a substantially regular concentration/flow profile of conjugate/fluid sample solution to each of the downstream sensor pads 45. The diffusion zones are important at ensuring that there is uniform and comprehensive dissolving of the conjugate into the sample fluid. The sensor pad 45 comprises an analyte-specific receptor material, (eg. an antibody, antigen, or MIP) immobilised on a carrier material. In various embodiments, a procedural control receptor (eg. a broad spectrum antibody or MIP, and/or antigen,) is positioned downstream from the analyte-specific receptor MIP. The procedural control may be included to ensure that (i) sample fluid has flowed past the analyte-specific receptor, (ii) the right conditions are present for binding of the target analytes and the analyte-specific receptors and/or (iii) the signal reader component of the apparatus 12 is functioning correctly. In one embodiment, when the fluid sample with dissolved conjugates arrives at each sensor pad 45, target analyte molecules in the fluid compete with their respective conjugate molecules for binding by the analyte-specific receptor sites of the MIP material. Target analytes and conjugates bind to the analyte-specific receptor sites and the procedural control receptor sites before flowing onwards. Remaining unbound conjugates are washed away through a second diffusion zone 44 towards the absorbent pad 46. Fluid flow terminates at a location downstream of the absorbent pad 46 where a channel vent 47 provides a capillary stop. One advantage of this approach is that the total fluid flow time, i.e., total assay time, measured is typically is about 30 sec, a value that represents a significant enhancement of assay speed when compared with the usual time durations of traditional flow immunoassays. Another advantage of employing reagent 43, sensor 45 and absorbent 46 pads that are introduced into the one or more channels 42 at appropriate locations in a discontinuous, non-contiguous manner, is that, in comparison with a traditional flow immunoassay, the quantity of porous materials employed within the fluid flow path, and, hence, the effective surface area in contact with the fluid sample during flow, can be much smaller. As a result, the levels of unwanted non-specific adsorption of target analytes onto the available pad and channel surfaces is expected to be significantly less pronounced. In various embodiments, this is a factor by which the system 10 facilitates the reliable detection of the presence of target analytes such as, e.g., drugs of abuse, given the low detection thresholds associated with such substances (typically less than 10 to 100 ng/ml).

In various embodiments, the reader 13 comprises a socket to receive the cartridge 11, a light delivery arm to direct excitation radiation through the cartridge inspection window 34 onto the sensor pad locations 45 in the fluidic chip 26, and a sensing arm to collect and detect fluorescence radiation from each of the sensor locations 45 in parallel, via the inspection window 34. In various embodiments, the analysis system is used with an apparatus 12 the mother instrument 12 which incorporates electronic circuitry with associated software to process the detected signal parameters to generate an immediate reading. In various embodiments, this reading may be of sufficient accuracy for initial screening at the scene, such as at a road checkpoint.

While the use of fluorescence detection is used as an exemplary detection means herein, it is to be understood that any detection means may be used. In particular, it will be appreciated that directly or indirectly detectable labels can be involved. For example, without limitation, besides fluorescent labels, other labels that can be read optically include gold or silver nanoparticles, which may be detected by light scattering, colorimetric means, etc These examples are in no way exhaustive, but simply illustrate a few of the labelling strategies that can be applied in various embodiments of the current invention.

With the cartridge 11 inserted into the reader 13, the module is closed to form a lightproof seal. In various embodiments, the module 13 directs an excitation beam of a specific wavelength at each of the sensor pad locations 45 within the one or more channels 42 of the fluidic chip 26 in order to excite the fluorescent dyes in the conjugates that have been bound at each sensor pad 45 during the assay. In various embodiments, the presence of target analyte within the fluid sample prevents binding of the fluorescent conjugates to the antibodies, antigens or molecularly imprinted polymers, According to such embodiments, the concentration of the target analyte is inversely related to the intensity of the fluorescence signal measured at the sensor pad 45. The resulting fluorescence signal arising at each sensor pad location 45 may then be measured and, for example, compared with previously measured and stored calibration data using an algorithm to produce an output electrical signal. In various embodiments, this signal is passed on to the apparatus 12 which can, for example, be used to produce a simple qualitative report regarding the presence or absence of the target analyte, or a fully quantitative report on the concentration of the target analyte within the fluid sample. In certain embodiments, multivariate methods could be applied to analysis of the fluorescence signal data to achieve quantification of different target analytes and to provide better distinction of false positives. While such an approach is well suited for the resolution of complex systems (eg, when multiple analytes are detected in a single channel), the use of a dedicated channel for each target analyte assay enables the use of simple chemometric principles.

In situations where the target analyte is present in concentrations that are significantly greater than the detection threshold concentration, a measurement result can then be reached rapidly, providing a useful early warning. For example, during a fluorescence-based competitive assay for a particular target analyte within a particular channel 42 of the fluidic chip 26, the rate of decrease of the fluorescence signal from the sensor pads can be readily measured by the reader 13. In various embodiments, for example when the kinetics of competitive, sandwich or other immunoassays may be difficult to control in a reproducible fashion, (eg. because they depend upon such factors as assay temperature, analyte and reagent concentrations, the degree of mixing of these species, etc.) each assay reaction may be allowed to proceed to equilibrium before undertaking subsequent signal acquisition and data processing steps. Other examples of labels which can also be optically read in alternate configurations include gold or silver nanoparticles, which may be detected by, for example, light scattering or colorimetric means. These examples are in no way exhaustive, but simply illustrate a number of labelling strategies that can be applied in various embodiments of the current inventions.

Referring again to FIGS. 4a and 4b, in various embodiments, following spreading of the conditioned, retrieved fluid sample across all of the channel inlet ports 41 the fluid subsequently wets and flows along the one or more fluidic channels 42 of the chip 26 by capillary action. Without wishing to be limited to any particular theory, each of the inlet ports 41 provides a large surface area for ease of fluid access and wetting and for initiation of laminar capillary flow of fluid along the channels 42. By selecting an inlet surface area to channel cross-section ratio of between about 5 and about 20, consistent induction of fluid flow into the channels 42 can be routinely achieved.

In various embodiments, the sensor pad may comprise two or more separate or: adjacent pads.

In various embodiments, the analyte-specific receptors and/or procedural control receptors may include a MIP receptor. In various embodiments, an antibody or antigen may be used as one or both of the receptors.

In various embodiments, an absorbent pad 46 may not be present, for example when the wicking action of pulling fluid towards the bottom of the channel is not required.

In various embodiments, the length of each diffusion zone 44 may be a determinant of the concentration profile of the conjugate within each fluid sample as it reaches its corresponding sensor pad 45 and the resulting analytical performance of each assay. In various embodiments, to ensure levels of assay performance and reproducibility suitable for detection of drugs of abuse in oral fluids, the length of the diffusion zone in each channel 42 is set to a value between about 0.5 mm and about 5 mm. Without wishing to be limited to any particular theory, combined with the rapid release of conjugate from each reagent pad 43 followed by equally rapid mixing with each fluid sample, the use of a short diffusion zone 44 can ensure that a tight, plug- or band-type, homogeneous concentration profile of conjugate within the conjugate/fluid sample solution arrives at each sensor pad 45. In various embodiments, this may facilitate increasing assay sensitivity and reproducibility.

Figure 4C:
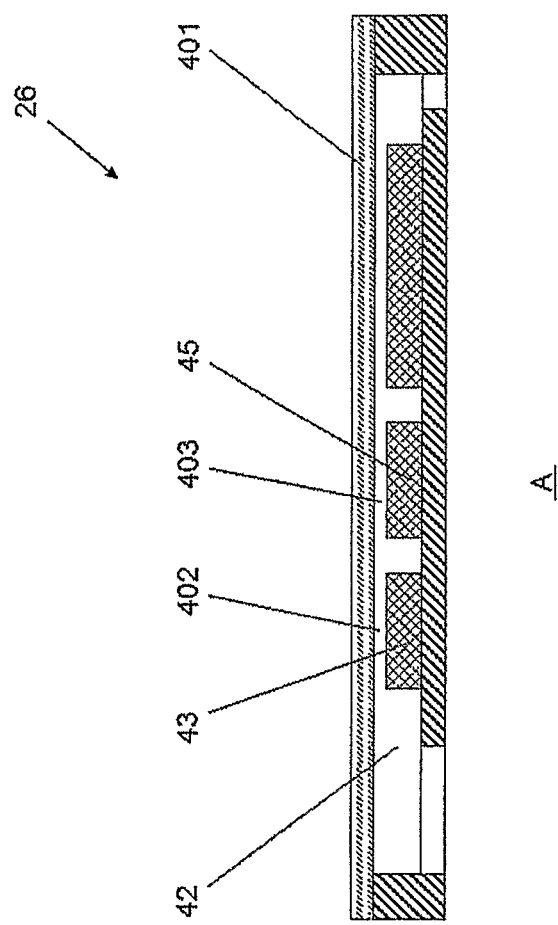
FIG. 4c shows a cross-sectional view along a channel of the fluidic chip.

Referring to FIG. 4c, a cross-sectional diagram of the fluidic chip 26 in FIG. 4a is shown. In this embodiment another aspect of the channels 42 is that there may be a gap 402 between the top surface of the reagent pad 43 and the upper channel wall as well as a gap 403 between the top surface of the sensor pad 45 and the upper channel wall. The upper channel wall is defined by a clear top layer 401 that covers the fluidic channel. Both gaps 402 and 403 have dimensions ranging from 0.05 mm to 0.5 mm. Within these dimensions a quantity of sample fluid is allowed to flow over each respective pad. While this quantity does not contribute to the sensing, it does assist flow along the channel by providing continuity along the channel and thus assists in capillary action. The gaps also provide a regulation of the sample fluid's flow rate. The exact dimensions of both gaps are selected against the viscosity of the intended sample fluids. To give an example, for a sample fluid with a viscosity of 5 the gap 402 above the reagent pad may be 0.05 mm, while the gap 403 above the sensor pad may be 0.25 mm. For the purposes of clarity the gaps 402 and 403 are exaggerated in FIG. 4c.

In various embodiments, the rate of flow of each conjugate/fluid sample solution is a determinant of the efficiency with which a target analyte and/or its respective conjugate binds to the receptors on its corresponding sensor pad 45, and the resulting analytical performance of each assay. In this regard, while increased fluid flow rates may decrease the levels of non-specific binding (background) subsequently measured at sensor pads 45, decreased fluid flow rates may increase the levels of measured signals at the expense of also increasing the levels of background.

To optimize the rate of flow of each conjugate/fluid sample solution across each corresponding sensor pad 45, and to thereby facilitate optimisation of the performance of each assay, fluid flow may be regulated during conjugate release by controlling the relative dimensions and porosity of the reagent pads 43. In various embodiments, the dimensions of each of the reagent pads 43 are selected such that the pads fill the complete width of each channel 42 with pad lengths of between about 2 mm and about 20 mm and height of pads between about 0.05 mm and 1 mm. In various embodiments, the mean size of the pores within the reagent pads 43 may be set at about 20 μm. In various embodiments, the mean size of the pores may range between about 5 μm and about 100 μm.

In various embodiments, the rate of fluid flow during the target analyte/conjugate binding stage may be also regulated by varying the relative dimensions and the porosity of the absorbent pads 46. In various embodiments, the dimensions of each of the absorbent pads 43 may be selected such that the absorbent pads fill the complete cross-section of each channel 42 with pad lengths of between about 3 mm and about 25 mm. In various embodiments, the mean size of the pores may range between about 1 μm and about 100 μm.

In various embodiments, the sensor pads 45 are integrated into the channels 42 in such a way that fluid flow between reagent pads 43 and absorbent pads 46 is not substantially impeded. For example, each of the sensor pads 45 may be placed into recesses formed in the channel bottom at specific locations along the length of each channel 42 so that only the top surface of each pad is exposed to the conjugate fluid sample solution. In various embodiments, the sensor pads 45 may be placed into each channel 42 so that a gap of between about 0.05 mm to about 0.5 mm between the top surface of each sensor pad 45 and the channel roof is provided. For example, nitrocellulose pads incorporating antibody or antigen receptors or for glass fibre pads bearing MIP receptors, the length of each of the sensor pads 45 could be set at between about 2 mm and about 20 mm.

In various embodiments, fluid flow may be regulated by setting the relative dimensions of the channel vents 47 with respect to the intended flow rate and viscosity of the sample fluid. For example, the diameter of a round channel vent 47 could be set to 0.8 mm for fluids with viscosities of 1-20 cp. However, irrespective of shape the size of the opening of the channel vents 47 may range from about 0.1 mm to 5 mm.

In various embodiments, fluid flow may be regulated either by setting the dimensions of each of the fluidic channels 42 of the chip 26 at various locations and/or by application of a surface treatment and/or by placement of pads of materials that impede fluid transport when wet, e.g., cotton, wool, etc., at appropriate locations inside a channel 42.

The ease of fluid retrieval by the cartridge 11 and of fluid flow through the channels 42, with pads 43, 45 and 46 in place, of the chip 26 may be illustrated by considering a variety of fluid types: pooled oral fluid, frozen for storage and thawed for use (viscosity near 1.0 cp); Pooled oral fluid, not frozen (viscosity near 1.0 cp); Artificial saliva with 2 mg/mL of hog gastric mucin (viscosity of approx. 1.4 cp); Aqueous buffer solutions spiked with drugs of abuse and various concentrations of bovine salivary mucin to tune viscosity from 1.0 cp to 7.2 cp; Glycerol in three dilutions providing increasing levels of viscosity from 12.79 cp, 20.61 cp to 37.15 cp, respectively. For example, when approximately 1.3 ml of oral fluid newly acquired from a donor on a swab was tested with an exemplary cartridge an average sample volume of 1.0 ml was retrieved by the cartridge 11, following less than 10 sec of compression, with the swab retaining the remainder of the sample. Using the fluids listed above we found that the cartridge 11 successfully transferred sufficient fluid samples from a swab 30 into channels 42 with the fluids flowing all the way through the reagent 43, sensor 45, and absorbent 46 pads, respectively in less than 30 sec.

The reagent pads 43 and the absorbent pads 46 may be made from, for example, glass fibre or other suitable absorbent porous material. The sensor pad 45, comprise substrates that may be made from, for example, nitrocellulose membranes, or other suitable materials, that incorporate immobilised antibodies and/or antigens and/or MIP particles, or porous or non-porous substrates that bear chemically grafted MIP layers. A porous substrate could, for example, be a macroporous, mesoporous or nanoporous oxide material, such as glass fibre, silicon dioxide, silica or alumina or another porous oxide material with a surface that can be activated to allow the attachment of initiator moieties for the initiation of a grafted MIP layer onto the substrate surface. In various embodiments, the chemically bonded thin polymer layer would have minimal swelling such that, e.g., MIP grafted substrates would be mechanically stable in different solvents, during operation and prolonged storage. In various embodiments, the thin grafted MIP layer does not interfere with transport and provides the desired chemical selectivity. In various embodiments, grafting of MIP to pad substrates in a thin layer provides a substantial reduction in the level of released template.

In certain embodiments, the use of porous pads in combination with fluidic channel may ensure good transport for viscous liquids and heterogeneous samples about and through such substrates. The fluid to be analysed must also pass over or through a pad, which may improve the speed of the analysis assay by concentrating the small amounts of materials involved onto a small area to facilitate subsequent highly sensitive detection. Pad substrates are also useful because they are amenable to further miniaturisation and generally have high mechanical and chemical stability. In various embodiments, the use of such substrates can also facilitate, e.g., processing of the pad material, and pad placement at desired locations within each channel 42 of the fluidic chip 26, using techniques that are amenable to cost-effective, high volume manufacturing, such as surface pre-treatment with reagents or other agents, for example, blocking agents, by dipping, vapour exposure, aerosol spraying or liquid droplet deposition, and pad positioning and assembly by pick-and-place methods. In various embodiments, one advantage of the use of pick-and-place methods for chip assembly is that known-good-pads, identified by pre-screening, may be selected for placement, thereby providing a way to maximise manufacturing yield. Pick-and-place methods are also compatible with rapid, automated optical inspection during manufacturing and with subsequent product miniaturisation.

To facilitate that accurate data signal measurements may be carried out at each active sensor location on the fluidic chip 26 using the reader 13, the chip 26 is equipped with a number of mechanical alignment features 48 that provide reproducible and robust registration with the internal mechanics of the detection module 13 by direct contact. Referring to FIG. 2, in the fluidic chip 26 may be integrated into the cartridge 11 by sandwiching it between planar seals 27, and the cartridge front 21 and rear 22. According to such embodiments, when the cartridge 11 is fully assembled, the chip 26 sits over the placement features 28, which precisely position the chip 26 within the extraction chamber 23. Referring to FIG. 4, the features 49 on the fluidic chip 26 may be designed to correspond to and match with the placement features 28 in order to facilitate the positioning of the chip 26 with respect to the extraction chamber 23. In turn, this positioning facilitates the mechanical alignment feature 48 on the fluidic chip 26 to protrude outside of the cartridge 11 thereby providing direct registration between the chip 26 and the reader 13.

Various aspects and embodiments of the present inventions may be illustrated by employing the convenient format of a flow-type assay whereby a fluid sample and the products of displacement, competition or sandwich affinity assays move through a fluidic chip, producing labelled zones that can be read by eye and/or by an optical transducer.

Figure 5A:
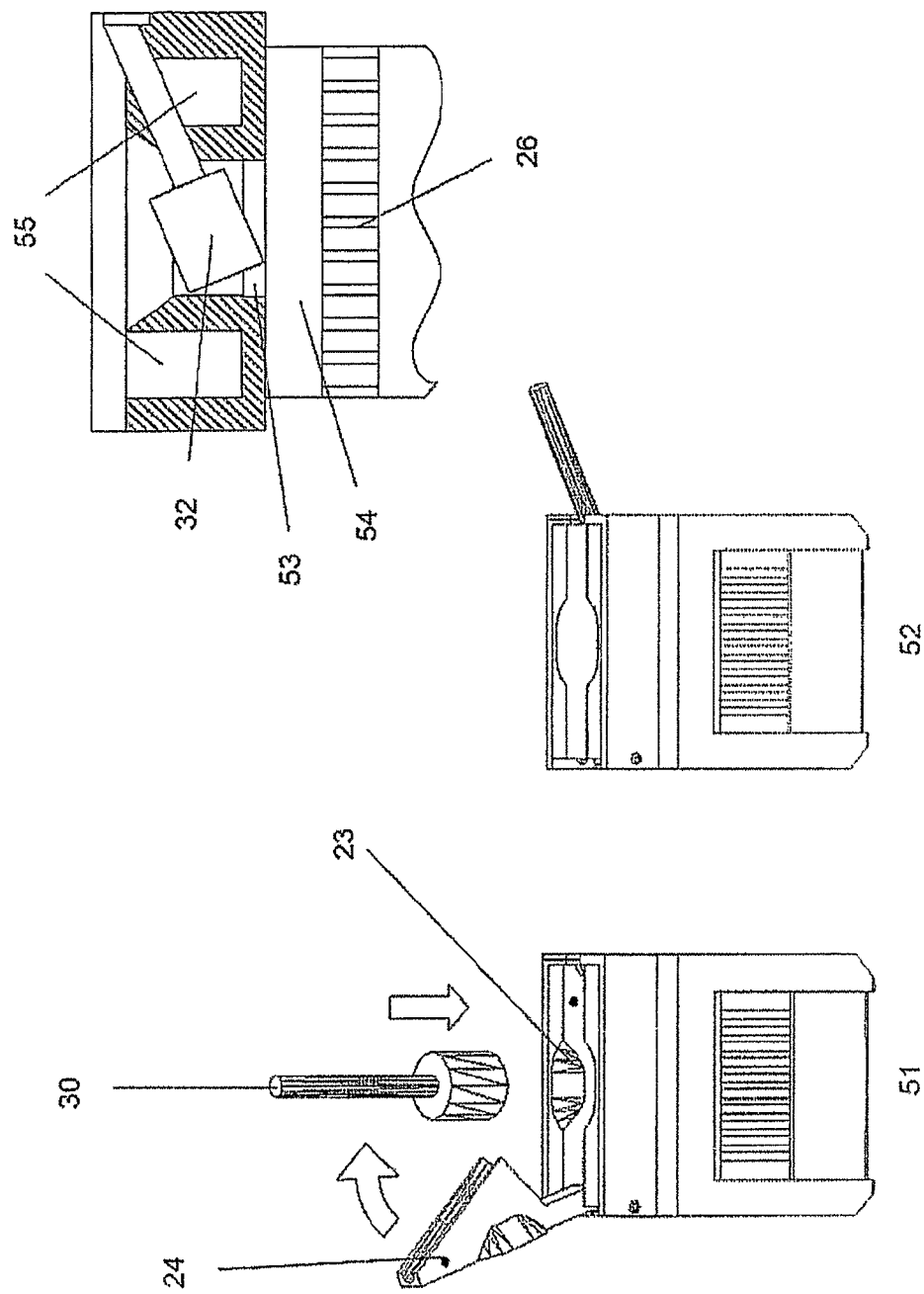
FIG. 5a is a set of perspective and cross-sectional views showing how a swab is inserted in a cartridge.

Referring to FIG. 5a, an exemplary cartridge 11 is shown standing upright with a swab 30 inserted into the extraction chamber 23 and with the hinged lid 24 in open 51 and closed 52 positions, respectively. To carry out a fluorescence-based assay using oral fluid, for example, a fluid sample of sufficient volume is collected by a swab 30. Upon insertion of the swab 30 into the extraction chamber 23 and closure of the hinged lid 24, the swab head 32 is compressed leading to the retrieval of sample fluid from the swab 30. The dimensions of the extraction chamber 23 are selected so that, when the lid 24 is closed upon the inserted swab 30, the foam/sponge head 32 is compressed to effectively release the fluid sample into the extraction chamber 23 and, at the same time, seal off any passage through which sample might flow in reverse. Also, when the lid 24 is fully closed and the swab head 32 is compressed, the head is in a tilted position that forces the retrieved fluid sample to drain off the head as defined droplets with limited bubble content. The retrieved fluid sample then passes from the extraction chamber 23, through a duct 53, into a draining chamber 54 that sits directly beneath the extraction chamber 23 and directly above the fluidic chip 26. In situations where excessive amounts of fluid are retrieved from the swab head 32, overflow reservoirs 55 adjacent to the extraction chamber 23 may capture any excess fluid present, preventing this fluid from draining through the duct 53. If desired, the configuration of the cartridge 11 may be easily modified so that a portion of a retrieved fluid sample may be routinely retained, without risk of cross-contamination, permitting further analysis of the sample in a laboratory at a later time.

Figure 5B:
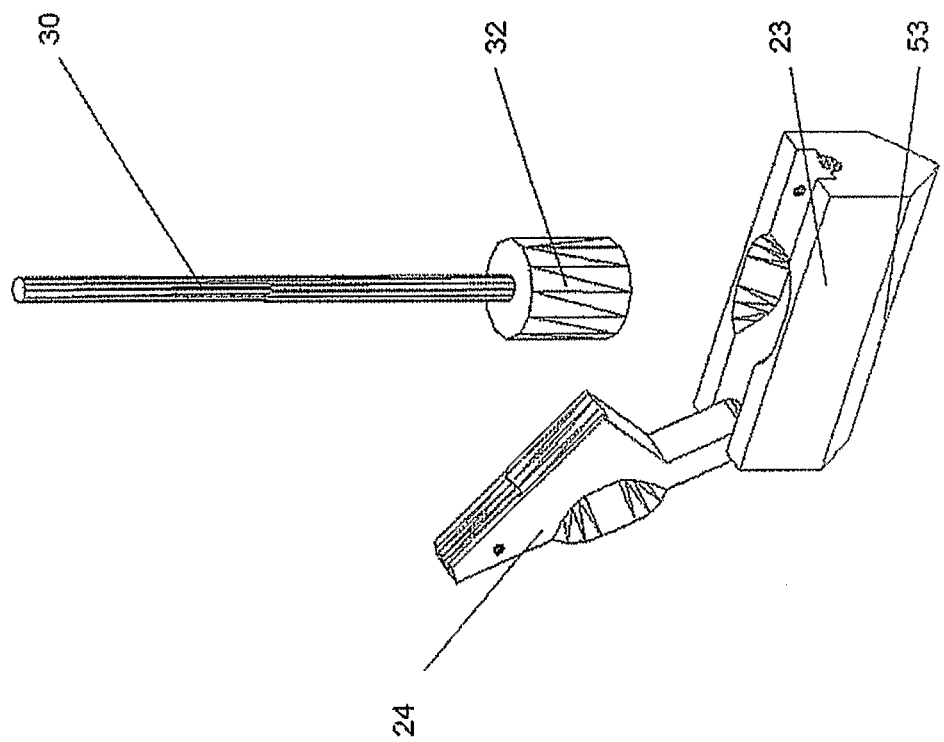

Referring to FIGS. 5a & 5b, the size and shape of the extraction chamber 23 is a determinant of the efficiency with which a fluid sample can be retrieved from a swab head 32 as well as of the efficiency with which the chamber 23 can be sealed against reverse fluid flow. Extraction efficiency can be enhanced where the extraction chamber 23 is equipped with a cavity that provides for the tightest possible confinement of the swab head 32. For example, in the uncompressed state, a typical, cylindrically shaped swab head 32 may have dimensions of 13 mm in diameter and 20 mm in length. In such a case, the dimensions of the cylindrical cavity inside the extraction chamber 23 could be set to between about 15 and about 20 mm in length and between about 4 mm and 8 mm in diameter to facilitate achieving effective retrieval of fluids with viscosities ranging between 1 and 20 cp. We have found that the angle at which the swab head 32 is tilted is generally a determinant of the efficiency with which droplets of retrieved fluid sample can form. In one example, by tilting the extraction chamber 26 at an angle of thirty degrees with respect to the vertical, retrieved fluids can routinely form droplets. The size and shape of the draining duct 53 may be a determinant of the efficiency with which a fluid sample can be retrieved from a swab head 32 and of the rate at which the retrieved fluid can pass from the extraction chamber 23 into the draining chamber 54. By using a duct with dimensions of about 10 mm to about 15 mm in length and about 1 mm and about 3 mm in width, efficient draining of retrieved fluid samples with viscosities ranging between about 1 cp and about 20 cp can be routinely achieved.

Figure 5C:
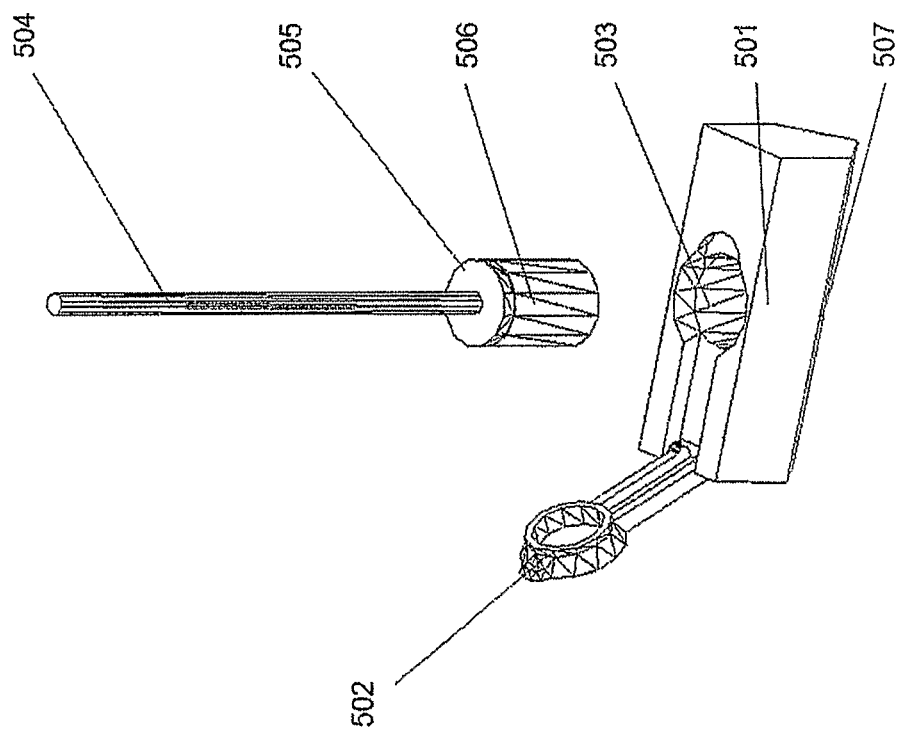

Referring to FIG. 5c, an alternative extraction chamber 501 is shown standing upright with a hinged lid 502 in an open position. The extraction chamber 501 is for use with a swab 504, whereby the foam head 506 is attached to a rigid or semi-rigid support 505 with a shape similar to the cross section of the foam head and a footprint equal or greater than the attached side of the foam head. Upon insertion of the swab 504 into the extraction chamber 501, sample fluid is retrieved from the swab 504 by a full compression of the foam head 506. Retrieved sample fluid passes through a duct 507 in the base of the cylindrical inlet 503 into the draining chamber 44 of the cartridge. Upon removal of the swab the hinged lid 502 is moved into closed position to seal the inlet cavity against reverse fluid flow.

The size and shape of the extraction chamber 501 may be a determinant of the efficiency with which a fluid sample can be retrieved from a swab head 506 as well as of the efficiency with which the chamber 501 can be sealed against reverse fluid flow. In various embodiments, extraction efficiency can be enhanced where the extraction chamber 501 is equipped with a cylindrical inlet cavity 503 that seals tightly around the foam head support 505 and provides for the tightest possible confinement of the foam head 506 upon insertion of the swab 504. For example, in the uncompressed state, a typical cylindrically-shaped swab head 506 may have dimensions of 13 mm in diameter and 20 mm in length with a round foam head support 1 mm in height and 13 mm in diameter. In such a case, the dimensions of the cylindrical inlet cavity 503 inside the extraction chamber 501 could be set to 10 in depth and 13 mm in diameter to facilitate achieving effective retrieval of fluids with viscosities ranging between 1 and 20 cp.

The size and shape of the draining duct 507 is a determinant of the efficiency with which a fluid sample can be retrieved from a swab head 504 and of the rate at which the retrieved fluid can pass from the extraction chamber 501 into the draining chamber 54. By using a duct with dimensions of 13 mm in length and 3 mm in width, efficient draining of retrieved fluid samples with viscosities ranging between 1 and 20 cp can be routinely achieved.

Figure 5D:
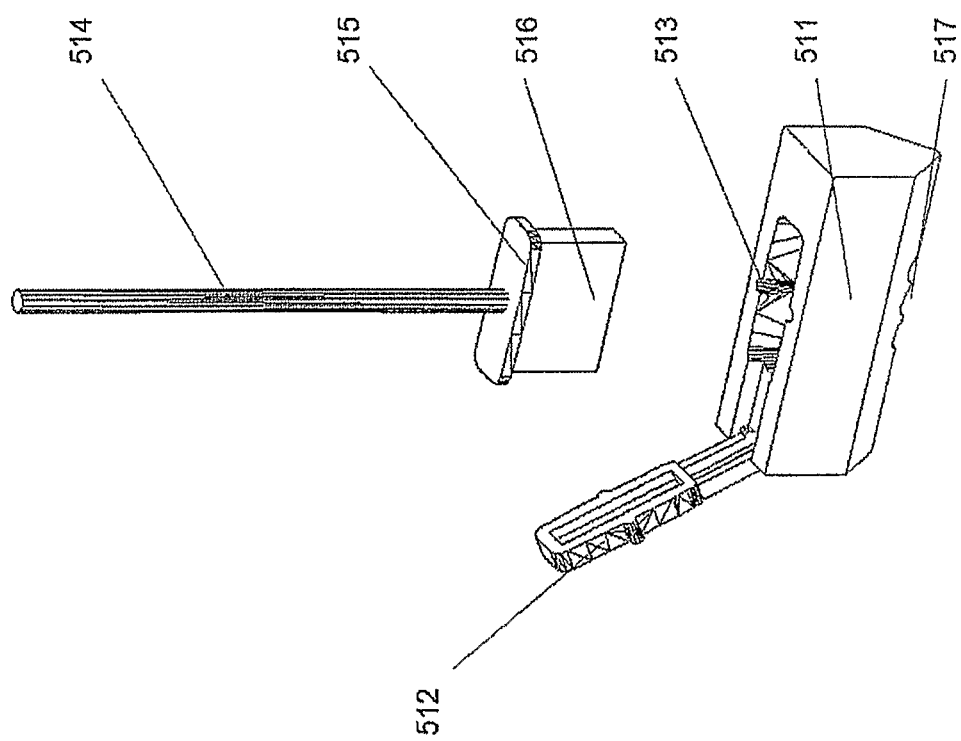

Referring to FIG. 5d, an extraction chamber 511 is shown standing upright with a hinged lid 512 in open position. The extraction chamber 511 is for use with a swab 514, whereby the foam head 516 is attached to a rigid or semi rigid support 515 with a shape similar to the cross section of the foam head and a footprint equal or greater than the attached side of the foam head. Upon insertion of the swab 514 into the extraction chamber, 511 sample fluid is retrieved from the swab 514 by a full compression of the foam head 516. Retrieved sample fluid passes through duct 517 in the base of the cuboid inlet, 513 into the draining chamber 44 of the cartridge 11. Upon removal of the swab the hinged lid 512 is moved into closed position to seal of the inlet cavity against reverse fluid flow.

The size and shape of the extraction chamber 511 may be a determinant of the efficiency with which a fluid sample can be retrieved from a swab head 516 as well as of the efficiency with which the chamber 511 can be sealed against reverse fluid flow. In various embodiments, extraction efficiency can be enhanced where the extraction chamber 511 is equipped with a cuboid inlet cavity 513 that seals tightly around the foam head support 515 and provides for the tightest possible confinement of the foam head 516 upon insertion of the swab 514. For example, in the uncompressed state, a typical cuboid shaped swab head 516 may have dimensions of 20 mm in length, 3 mm in width and 25 mm in height with a flat foam head support of 21 mm in length, 4 mm in width and 1 mm in height. In such a case, the dimensions of the cuboid inlet cavity 513 inside the extraction chamber 511 could be set to 21 mm in length, 4 mm in width and 17 mm in height to facilitate achieving effective retrieval of fluids with viscosities ranging between 1 and 20 cp.

The size and shape of the draining duct 517 may be a determinant of the efficiency with which a fluid sample can be retrieved from a swab head 514 and of the rate at which the retrieved fluid can pass from the extraction chamber 511 into the draining chamber 54. By using a duct that comprises of 3 adjacent holes with a diameter of 4 mm efficient draining of retrieved fluid samples with viscosities ranging between 1 and 20 cp can be routinely achieved.

Figure 5E:
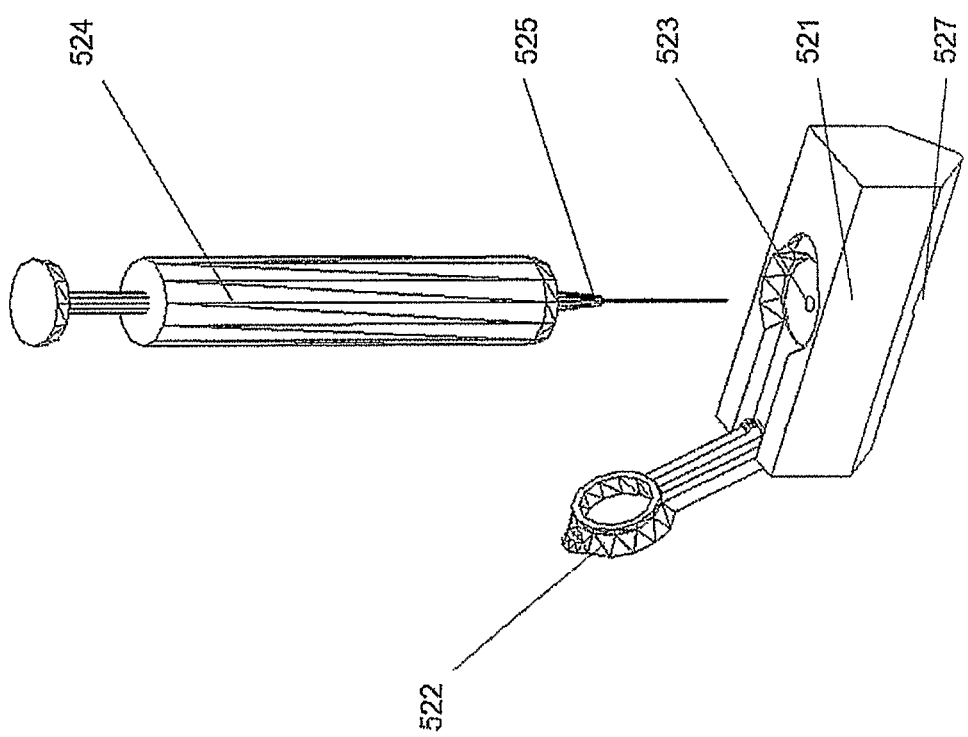

Referring to FIG. 5e, an extraction chamber 521 is shown standing upright with a hinged lid 522 in an open position. The extraction chamber 521 is apposite for syringe type collection devices 524 using hypodermic needles 525. The extraction chamber 521 contains a septum inlet 523, whereby the rubberised membrane partitions the inside of the extraction chamber 521 from the outside. Sample fluid can be transferred from the syringe 524 into the extraction chamber by piercing the needle 525 through the septum inlet 523 and by injecting the sample fluid. The transferred sample fluid passes through duct 527 in the base of the septum inlet 523 into the draining chamber 44 of the cartridge 11. Upon removal of the needle 525 the hinged lid 522 is moved into closed position.

Figure 5F:
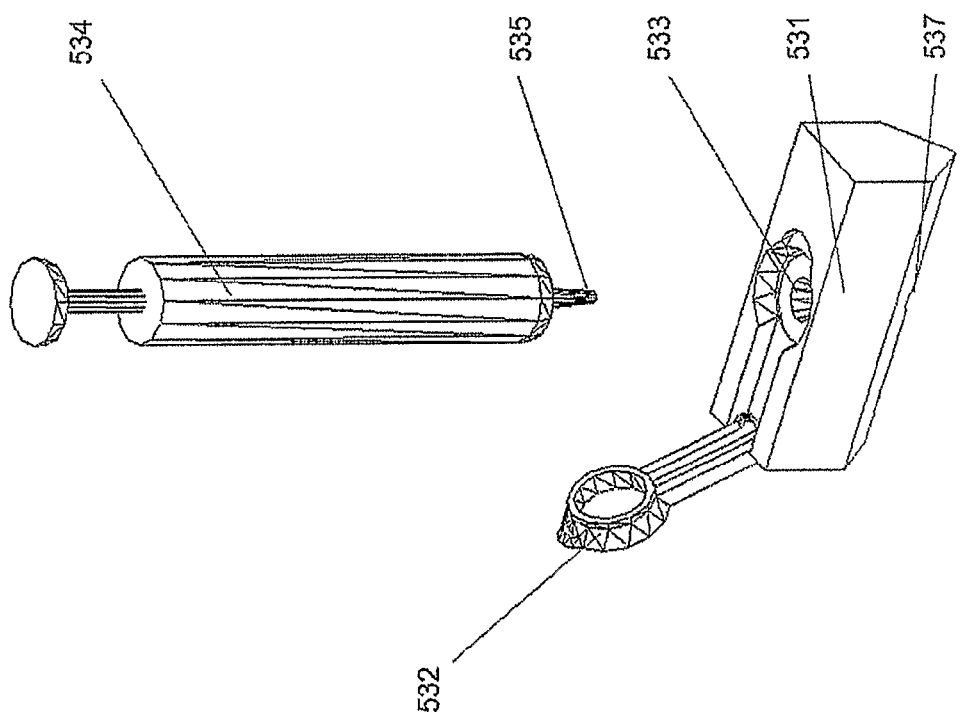

Referring to FIG. 5f, an extraction chamber 531 is shown standing upright with a hinged lid 532 in an open position. The extraction chamber 531 is apposite for syringe type collection devices. The extraction chamber 531 contains a coned inlet 533 that matches the shape of the syringe's nozzle 535 to form a tight seal when the nozzle is inserted into the inlet. Sample fluid can be transferred from the syringe 534 into the extraction chamber by inserting the nozzle of the syringe into the coned inlet 533 and by injecting the sample fluid. The transferred sample fluid passes through duct 537 in the base of the coned inlet 533 into the draining chamber 44 of the cartridge 11. Upon removal of the syringe 534 the hinged lid 532 is moved into closed position to seal of the inlet cavity.

Figure 5G:
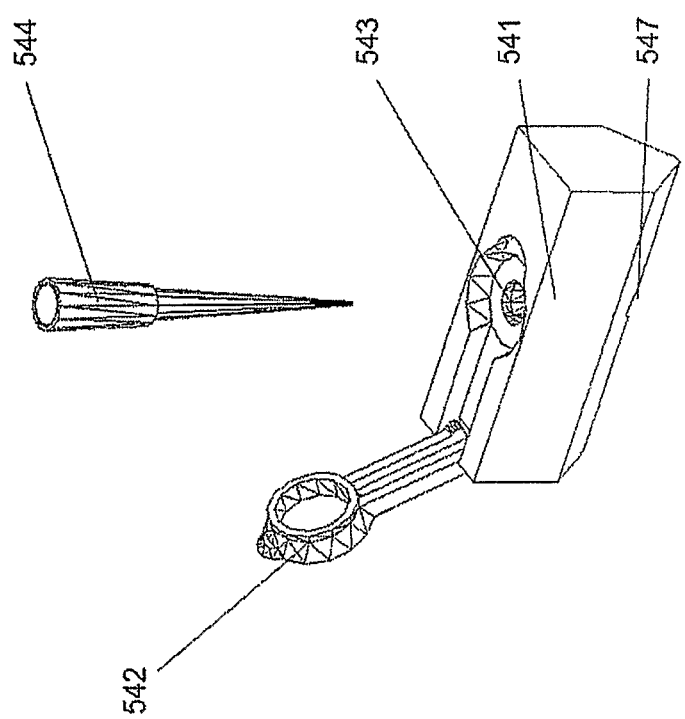

Referring to FIG. 5g, an extraction chamber 541 is shown standing upright with a hinged lid 542 in an open position. The extraction chamber 541 is apposite for pipette type collection devices. The extraction chamber 541 contains a cylindrical inlet 543 that provides a vertical extension to the duct 547 in the base of the extraction chamber 541. Sample fluid can be transferred from a pipette into the extraction chamber by inserting the pipette tip 544 into the inlet 543 and by injecting the sample fluid. The transferred sample fluid passes directly through the duct 547 in the base of the inlet 543 into the draining chamber 44 of the cartridge 11. Upon removal of the pipette tip 544 the hinged lid 542 is moved into closed position to seal of the inlet cavity.

Referring to FIG. 5h, an extraction chamber 551 is shown standing upright with a hinged lid 552 in an open position. The extraction chamber 551 is apposite for connectorised tubings 554, i.e. catheters, by providing a threaded inlet 553. Sample fluid can be transferred from a tubing 554 into the extraction chamber 551 by inserting the threaded connector 555 into the inlet 553 and by injecting the sample fluid. The transferred sample fluid passes through duct 557 in the base of the inlet 553 into the draining chamber 44 of the cartridge 11. Upon removal of the connector 555 the hinged lid 552 is moved into closed position to seal of the inlet cavity.

It is envisaged that a cartridge may have a combination of different inlet arrangements, for more versatility.

Referring to FIGS. 5a and 6a, the cartridge is shown upright in cross-sectional diagrams, with one diagram A detailing a cross-section along one channel 42 of the fluidic chip 26, and one diagram B detailing a cross-section in between two channels 42 of the fluid chip 26. Upon compression of a fluid-laden swab head 32 following closure of the hinged lid 24, the retrieved fluid sample passes from the extraction chamber 23, through the draining duct 53, into the draining chamber 54 prior to entering into the distribution chamber 40 of the fluidic chip 26. The draining chamber 54 conditions the fluid sample to facilitate providing uninterrupted, uniform sample flow into and through all of the channels 42 of the fluidic chip 26. This conditioning process involves the segregation of bubbles and solid impurities from the fluid sample and also a quick and uniform distribution of sample across all channel inlets. This is achieved by means of a split level design that divides the draining chamber 54 into a major top reservoir 61 and minor bottom reservoir 62.

The segregation of bubbles occurs inside the top reservoir 61 by allowing the bubbles to rise upwards and accumulate as foam at the top of the reservoir while, the fluid accumulates at the reservoir base. This action is assisted because there is a large volume in the top reservoir 61. In various embodiments, the removal of solid impurities occurs in three stages during the process of sample transfer through the cartridge 11. In the first instance the largest impurities are removed as the sample passes from the extraction chamber 23 through the draining duct 53 into the draining chamber's top reservoir 61, with the size and shape of the draining duct 53 determining the size of impurities being withheld. The second removal of impurities takes place at the intersection of distribution chamber 40 and channels 42 of the fluidic chip 26, with the dimensions and shape of the channel cross section determining the size of impurities being withheld. By selecting the width of the opening to be equal to that of the fluidic channel 42 and a combined depth of channel and bottom reservoir of between about 0.5 mm and about 1.5 mm, effective extraction and retention of solid impurities within the top reservoir 61 can be routinely achieved. The third and stage, removing more of the fine impurities is achieved through the reagent pads 43, with the pads porosity determining the size of impurities being withheld.

The narrow profile of the bottom reservoir 62 facilitates conditioning of the fluid sample, and thus quick and even filling of the distribution chamber 40 of the fluidic chip 26. The cross-sectional diagram B shows the distribution chamber 40 is shallow in the $3^{rd}$ direction but elongated in the $2^{nd}$ direction along the top of the channels 42 for effective spreading into the channels 42. Quick spreading (in 1 to 2 sec) of the fluid across all of the channel inlet ports 41 results in timely, uniform filling of all of the fluidic channels 42 of the chip 26. The dimensions of the bottom reservoir 62 may be a determinant of the overall effectiveness of the conditioning process and of the uniformity with which the filling of the fluidic channels 42 subsequently occurs. By selecting the width of the bottom reservoir 62 to be substantially equal to that of the fluidic chip 26, the height to be substantially equal to the length of the sample inlet ports 41 of the chip 26 and the depth to be between about 0.25 mm and about 2 mm, uniform capillary filling of the fluidic channels 42 by conditioned, retrieved fluid samples with viscosities ranging between 1 and 20 cp can be routinely achieved.

Figure 6B:
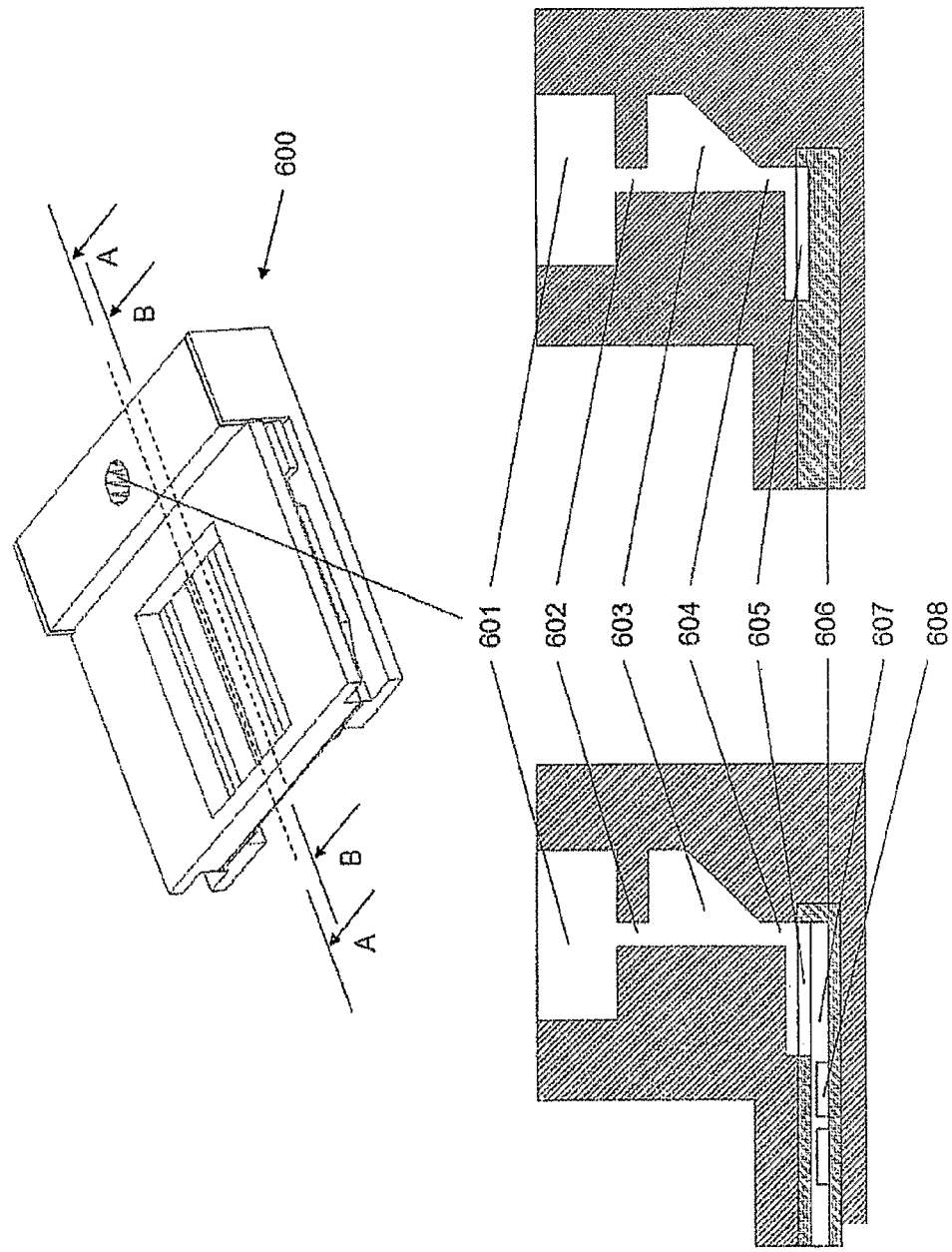
FIG. 6b shows a further arrangement of the cartridge.

Referring to FIG. 6b, a cartridge 600 is shown upright in perspective and cross-sectional diagrams, with one diagram A detailing a cross-section along one channel 607 of the fluidic chip 606, and one diagram B detailing a cross-section in between two channels 607 of the fluid chip 606. In this embodiment the fluidic chip 606, an embodiment of the fluidic chip 26, sits horizontally inside the cartridge 600, with the chip's distribution chamber 605 spatially aligned to the cartridges's 600 bottom reservoir 604.

Upon transfer of a fluid sample from a suitable collection device retrieved fluid passes from the extraction chamber 601, through the draining duct 602, into the device's draining chamber. The segregation of bubbles occurs inside the draining chamber's top reservoir 603 by allowing the bubbles to rise upwards and accumulate as foam at the top of the reservoir 603 while the fluid accumulates at the reservoir base.

The removal of solid impurities occurs in three stages during the process of sample transfer through the cartridge 600. In the first instance the largest impurities are removed as the sample passes from the extraction chamber 601 through the draining duct 602 into the draining chamber top reservoir 603, with the size and shape of the draining duct 602 determining the size of impurities being withheld. The second removal of impurities takes place at the intersection of distribution chamber 605 and channels 607 of the fluidic chip 606, with the dimensions and shape of the channel cross section determining the size of impurities being withheld. By selecting the width of the opening to be equal to that of the fluidic channel 607 and a combined depth of channel and bottom reservoir of between 0.5 mm and 1.5 mm, effective extraction and retention of solid impurities within the top reservoir 603 can be routinely achieved. The third and most detailed removal of fine impurities is achieved through the reagent pads 608, with the pads porosity determining the size of impurities being withheld.

The narrow profile of the bottom reservoir 604 facilitates conditioning of the fluid sample, and thus quick and even filling of the distribution chamber 605 of the fluidic chip 606. The cross-sectional diagram B shows the distribution chamber 605 is shallow in the $3^{rd}$ direction but elongated in the second direction along the top of the channels 42 for effective spreading into the channels 42.

In the embodiment of FIG. 6b, the sequence of sample fluid flow in the first, second, and third directions still applies. However, upon moving in the third direction, it continues in the third direction along the channels, whereas in the FIG. 6a embodiment, it changes back to the first direction to flow along the channels.

Quick spreading (in about 1 to 2 sec) of the fluid across all of the channel inlet ports 41 can subsequently results in timely, uniform filling of all of the fluidic channels 607 of the chip 600. The dimensions of the bottom reservoir 604 are a determinant of the overall effectiveness of the conditioning process and of the uniformity with which the filling of the fluidic channels subsequently occurs. By selecting the width of the bottom reservoir 604 to be substantially equal to that of the fluidic chip 606, the height to be substantially equal to the length of the sample inlet ports 41 of the fluidic chip 600 and the depth to be between about 0.25 mm and about 2 mm, uniform capillary filling of the fluidic chip's 606 channels by conditioned, retrieved fluid samples with viscosities ranging between 1 and 20 cp can be routinely achieved.

Figure 7A:
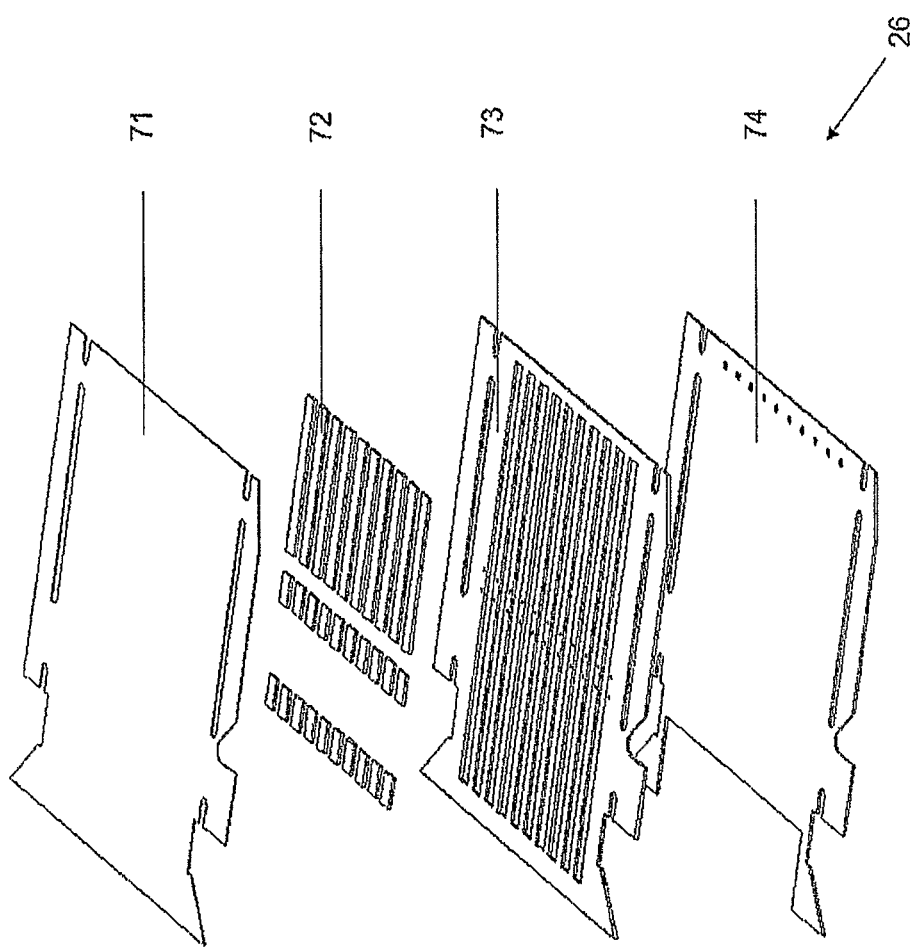
FIG. 7a is an exploded views of the fluidic chip.
Figure 7B:
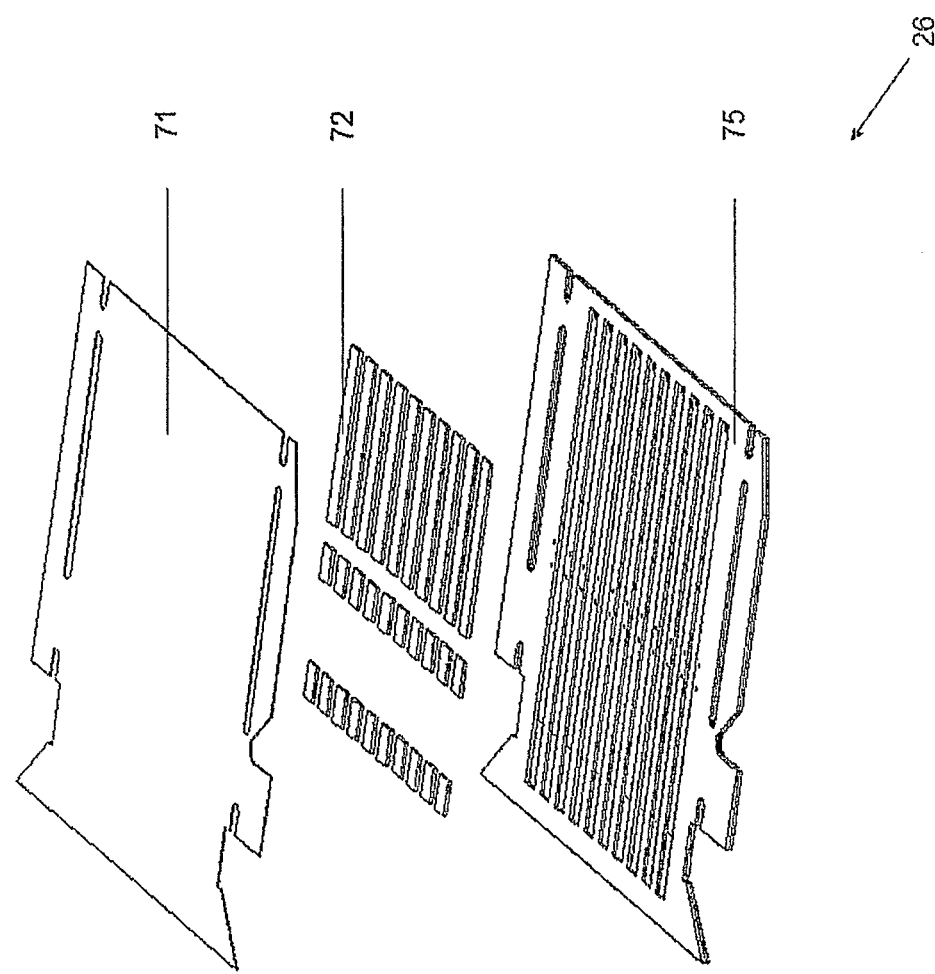
FIG. 7b is an exploded view showing an alternative way of manufacturing the chip.

Referring to FIGS. 7a and 7b, in various embodiments, fluidic chips 26 may be fabricated (FIG. 7a) by laminating multiple planar layers comprising a support layer 74, a layer 73 with through-cut channel and well features, and an optically clear top layer 71. Reagent, sensor and absorbent pads 72 may be introduced into the channels 42 at appropriate locations, and in a discontinuous, non-contiguous manner, prior to lamination of the top layer 71, and may be fixed in place during the lamination process. To provide fluid flow into the channels 42, entry ports may be formed in each laminated structure either at the edges or through the support layer 74 or top layer 71. While there are only five channels illustrated, the fluidic chip may incorporate a different number of channels. In various embodiments, fluidic chips 26 may be fabricated (FIG. 7b) by injection moulding a support plate 75 with embedded channel structures. Reagent, sensor and absorbent pads 72 may be introduced into the channels 42 at appropriate location's, and in a discontinuous, non-contiguous manner, prior to lamination of the top layer 71, and may be fixed in place during the lamination process.

Figure 8A:
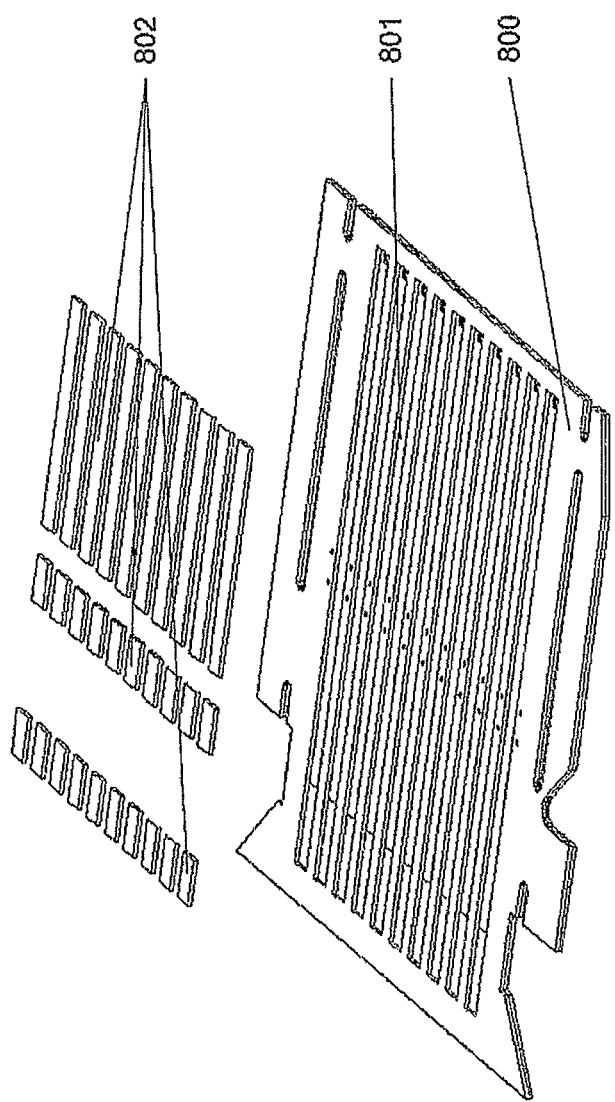
FIGS. 8a to 8g are diagrams showing alternative fluidic chip arrangements.

Referring to FIG. 8a, in various embodiments, reagent, sensor and absorbent pads 802 are integrated into the channels 801 of a fluidic chip 800 as discretely spaced entities at appropriate locations in a discontinuous, non-contiguous manner, through suitable assembly techniques.

Figure 8B:
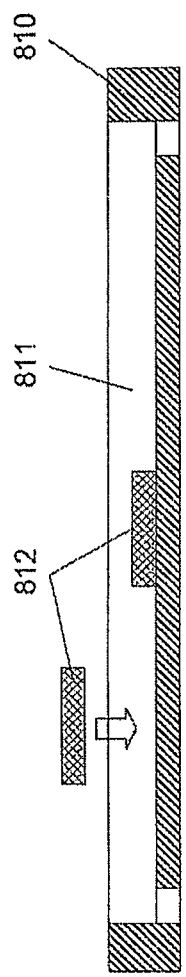

Referring to FIG. 8b, a fluidic chip 810 has integrated pads, whereby the reagent, sensor and absorbent pads 812 are held in place in discrete and separate positions at appropriate locations in a discontinuous, non-contiguous manner, via the surrounding walls of the fluidic channel 811.

Figure 8C:
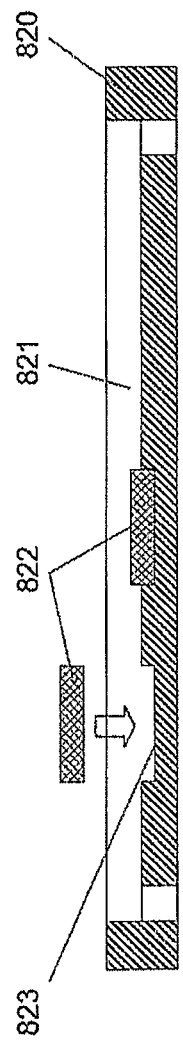

Referring to FIG. 8c, in a fluidic chip 820 the reagent, sensor and absorbent pads 822 are held in place in discrete and separate positions at appropriate locations in a discontinuous, non-contiguous manner, via recesses, which form part of the channel structure 821 and which accommodate part of the pad structure 822. Said recesses may be part of the horizontal or vertical or horizontal and vertical channel walls 821. The recesses have typical dimensions in the range of about 0.1 mm to about 1 mm in width, about 0.05 mm to about 1.00 mm in height and about 1 mm to about 50 mm in length.

Figure 8D:
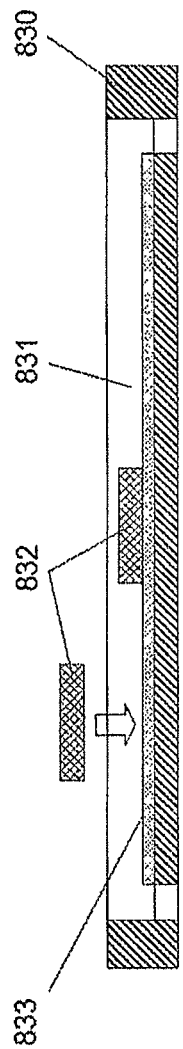

Referring to FIG. 8d, a fluidic chip 830 has reagent, sensor and absorbent pads 832 held in place in discrete and separate positions at appropriate locations in a discontinuous, non-contiguous manner, via a continuous adhesive coating 833, which forms part of the base of the channel structure 831.

Figure 8E:
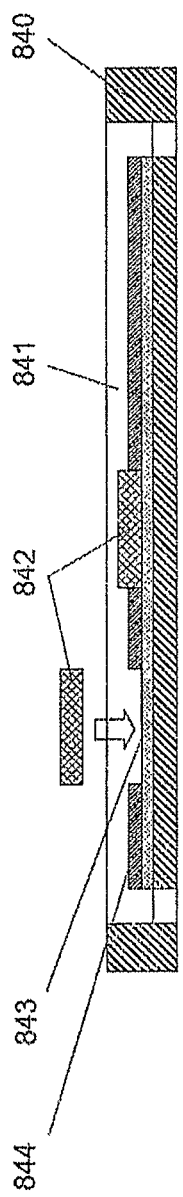

Referring to FIG. 8e, in a fluidic chip 840 the reagent, sensor and absorbent pads 842 are held in place in discrete and separate positions at appropriate locations in a discontinuous, non-contiguous manner, inside recesses 843, which have an adhesive coating at their base, and which form part of the channel structure 841. The recesses may be formed by means of a nonporous mask 844 directly applied onto the adhesive coating, with spaces provided in this masks with typical dimensions in the range of about 0.1 mm to about 1 mm in width, about 0.05 mm to about 1.00 mm in height and about 1 mm to about 50 mm in length.

Figure 8F:
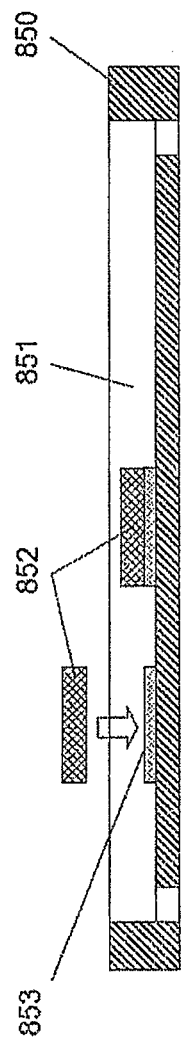

Referring to FIG. 8f, in a fluidic chip 850 reagent, sensor and absorbent pads 852 are held in place in discrete and separate positions at appropriate locations in a discontinuous, non-contiguous manner, via single or multiple discontinuous areas of adhesive coatings 853, which form part of the channel structure 851. In various embodiments, said coatings have typical dimensions in the range of about 0.25 mm to about 5 mm in width and about 0.5 mm to about 25 mm in length.

Figure 8G:
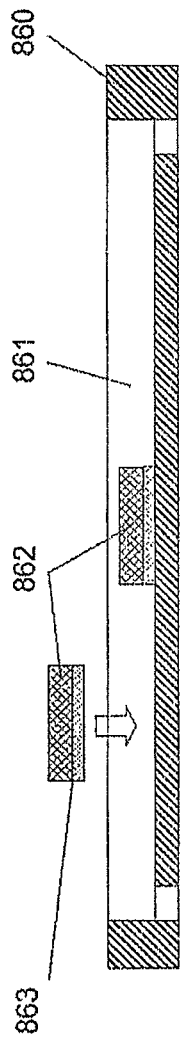

Referring to FIG. 8g, in a fluidic chip 860 reagent, sensor and absorbent pads 862 are held in place in discrete and separate positions at appropriate locations in a discontinuous, non-contiguous manner, inside the fluidic channel 861 through an adhesive coating on the underside of each individual pad 863.

Figure 9A:
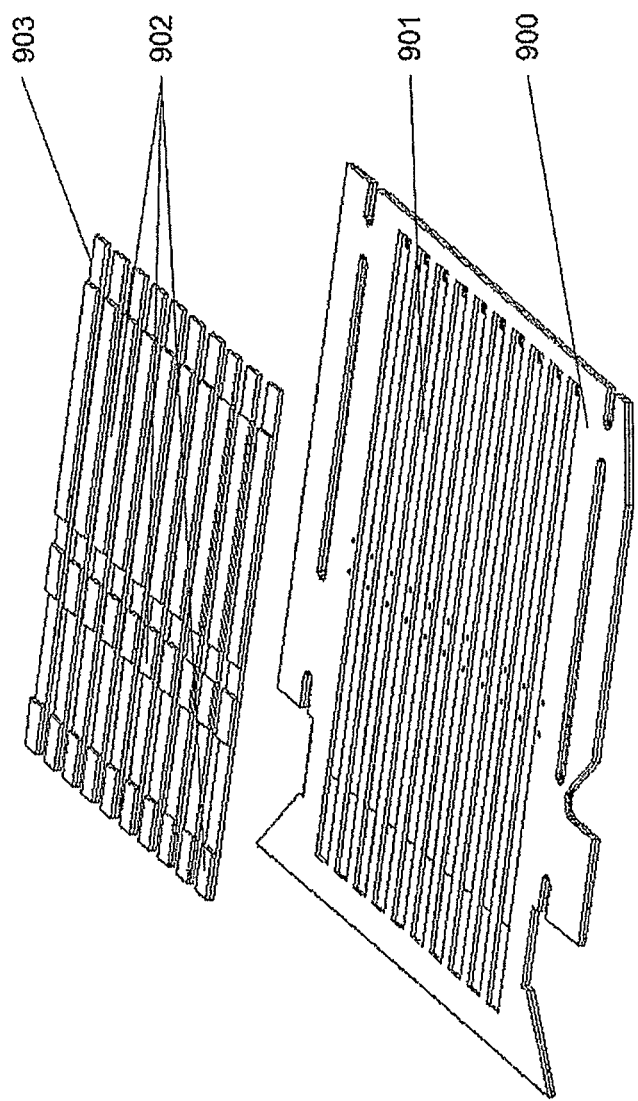

Referring to FIG. 9a, reagent, sensor and absorbent pads 902 are integrated into the channels 901 of the fluidic chip 900 as part of the assembly 903. Said supporting assembly 903 consists of a non-porous material. The reagent, sensor and absorbent pads 902 are attached to the supporting assembly 903 as discretely spaced entities at appropriate locations in a discontinuous, non-contiguous manner, through suitable assembly techniques. In various embodiments, said supporting assembly 903 has a strip format with typical dimensions in the range of about 1.3 mm to about 5 mm in width, about 0.05 mm to about 1.00 mm in height and about 5 mm to about 50 mm in length.

Referring to FIG. 9b, the pad supporting assembly 911 is an embodiment of the assembly 903, whereby the reagent, sensor and absorbent pads 912 are attached onto the assembly in discrete and separate positions at appropriate locations in a discontinuous, non-contiguous manner, by means of suitable bonding techniques, for example drying, annealing etc.

Referring to FIG. 9c, in a pad supporting assembly 921, reagent, sensor and absorbent pads 922 are attached onto the assembly in discrete and separate positions at appropriate locations in a discontinuous, non-contiguous manner, through recesses, which form part of the support assembly's structure 921 and which accommodate part of the pad structure 922. Said recesses may be in the horizontal or vertical plane or in both the horizontal and vertical plane. In various embodiments, said recesses have typical dimensions in the range of about 0.1 mm to about 1 mm in width, about 0.05 mm to about 1.00 mm in height and about 1 mm to about 50 mm in length.

Referring to FIG. 9d, in a pad supporting assembly 931 the reagent, sensor and absorbent pads 932 are attached onto the assembly in discrete and separate positions at appropriate locations in a discontinuous, non-contiguous manner, via a continuous adhesive coating 933 which forms part of the base of the support structure 931.

Referring to FIG. 9e, in a pad supporting assembly 941 reagent, sensor and absorbent pads 942 are attached in discrete and separate positions at appropriate locations in a discontinuous, non-contiguous manner, inside recesses 943, which have an adhesive coating at their base, and which form part of the support structure 941. Said recesses may be formed by means of a nonporous mask 944 directly applied onto the adhesive coating, with spaces provided in this masks with typical dimensions in the range of about 0.1 mm to about 1 mm in width, about 0.05 mm to about 1.00 mm in height and about 1 mm to about 50 mm in length.

Referring to FIG. 9f, in a pad supporting assembly 951 the reagent, sensor and absorbent pads 952 are attached in discrete and separate positions at appropriate locations in a discontinuous, non-contiguous manner, via single or multiple discontinuous areas of adhesive coatings 953, which form part of the support structure 951. Said coatings have typical dimensions in the range of 0.25 mm to 5 mm in width and 0.5 mm to 25 mm in length.

Referring to FIG. 9g, in a pad supporting assembly 961 the reagent, sensor and absorbent pads 962 are attached onto the assembly in discrete and separate positions at appropriate locations in a discontinuous, non-contiguous manner, through an adhesive coating on the underside of each individual pad 963. Said coatings have typical dimensions in the range of about 0.25 mm to about 5 mm in width and about 0.5 mm to about 25 mm in length.

Referring to FIG. 10a, a pad supporting assembly 1012 is integrated into the channels 1011 of the fluidic chip 1010 by means of suitable assembly techniques. The support assembly 1012 is held in place via the surrounding walls of the fluidic channel 1011.

Referring to FIG. 10b, a pad supporting assembly 1022 is integrated into the channels 1021 of the fluidic chip 1020 by means of suitable assembly techniques. The support assembly 1022 is held in place via recesses, which form part of the channel structure 1021 and which accommodate part of the pad assembly structure 1022. Said recesses may be part of the horizontal or vertical or horizontal and vertical channel walls 1021. In various embodiments, said recesses have typical dimensions in the range of about 0.1 mm to about 2 mm in width, about 0.05 mm to about 1.00 mm in height and about 1 mm to about 50 mm in length.

Referring to FIG. 10*c*, in various embodiments, the pad supporting assembly 1032 is integrated into the channels 1031 of a fluidic chip 1030 by means of suitable assembly techniques. The support assembly 1032 is held in place via a continuous adhesive coating 1033 which forms part of the base of the channel structure 1031. In various embodiments, said coatings have typical dimensions in the range of about 0.25 mm to about 5 mm in width and about 0.5 mm to about 25 mm in length.

Figure 10D:
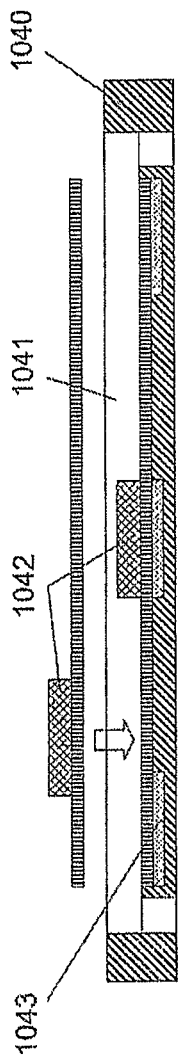

Referring to FIG. 10*d*, a pad supporting assembly 1042 is integrated into the channels 1041 of a fluidic chip 1040 by means of suitable assembly techniques. The support assembly 1042 is held in place in discrete and separate positions inside recesses 1043, which have an adhesive coating at their base, and which form part of the channel structure 1041. Said recesses have typical dimensions in the range of about 0.1 mm to about 5 mm in width, about 0.05 mm to about 1.00 mm in height and about 1 mm to about 25 mm in length.

Figure 10E:
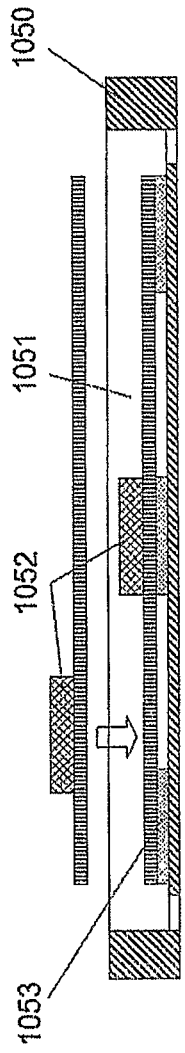

Referring to FIG. 10*e*, a pad supporting assembly 1052 is integrated into the channels 1051 of a fluidic chip 1050 by means of suitable assembly techniques. The support assembly 1052 is held in place via single or multiple discontinuous areas of adhesive coatings 1053, which form part of the channel structure 1051. Said coatings have typical dimensions in the range of 0.25 mm to 5 mm in width and 0.5 mm to 25 mm in length.

Figure 10F:
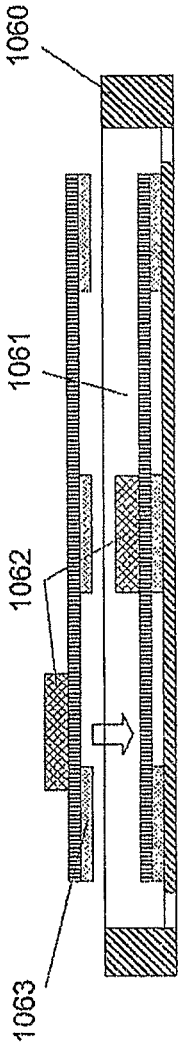

Referring to FIG. 10*f*, a pad supporting assembly 1062 is integrated into the channels 1061 of a fluidic chip 1060 by means of suitable assembly techniques. The support assembly 1062 is held in place through a single or multiple adhesive coating on the underside of each support assembly 1063. Said coatings have typical dimensions in the range of about 0.25 mm to about 5 mm in width and about 0.5 mm to about 50 mm in length.

Figure 11:
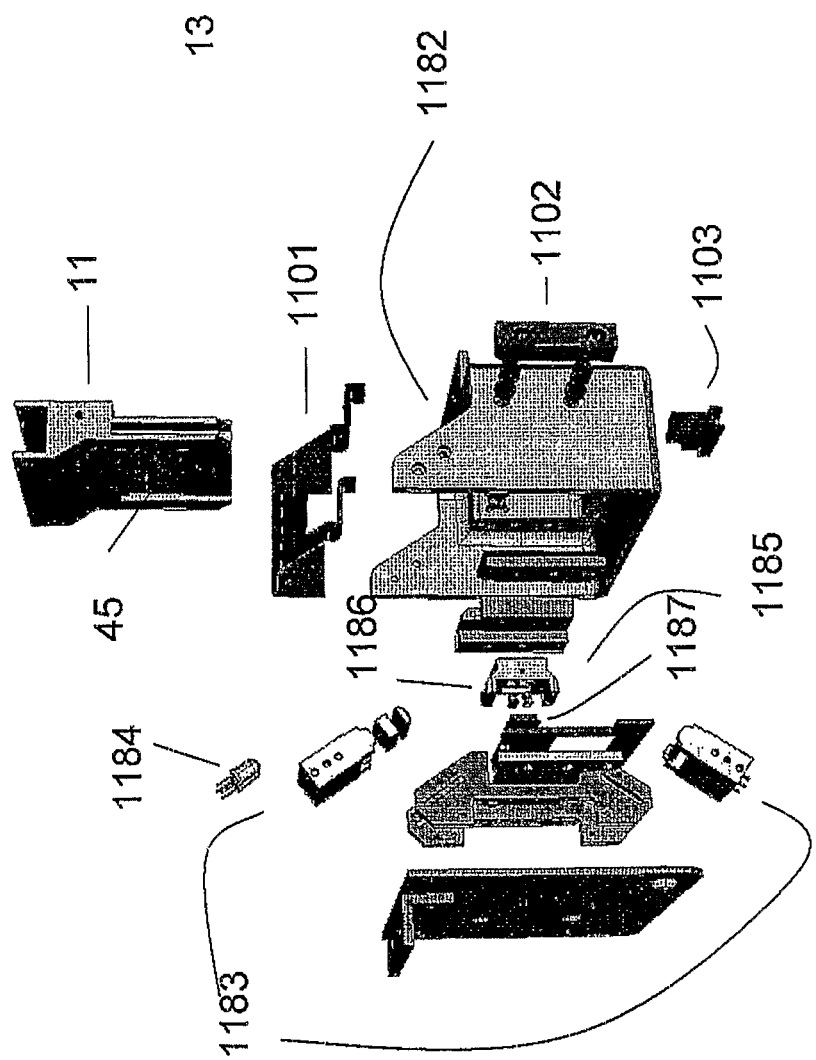
FIG. 11 is an exploded view of the optical detection reader of the system of FIG. 1.

FIG. 11 is an exploded diagram illustrating an exemplary reader 13. It comprises a mechanical assembly 1182 that receives and aligns the cartridge 11, one or two light delivery arms 1183 which contain sources of radiation 1184, a sensing arm 1185, and, also, electronic circuitry to amplify and/or pre-process the detected signals. In operation, the cartridge 11 is introduced into the reader 13 via a socket in the mother instrument 12. The mechanical assembly 1182 receives and aligns the cartridge 11 so that one or more rows of sensor pads 45 are in precise alignment with the light delivery 1183 and sensing 1185 arms, and so that the cartridge 11 can only be removed by pulling it with a force exceeding a certain threshold. The light delivery arm 1183 contains an array of sources of radiation 1184 to excite the fluorescent target-linker-label conjugates that may have become bound at each of the sensor pads 45 during an assay. These sources of radiation may include, for example, compact semiconductor lasers or light emitting diodes with wavelengths of emission that are appropriate for excitation of the fluorescent dyes. One skilled in the art can recognise that a plurality of beam shaping and conditioning optical components, including, for example, optical diffusers, integrated lenses and apertures may be included in the light delivery arm 1183 to achieve homogenuous illumination of one or more rows of sensor pads 45. The sensing arm 1185 contains light collecting optics 1186, which could, for example, comprise of a lens and/or pinhole array arrangement, an optical filter 1187, and light detecting elements, which could include photodiodes, photo integrated circuits, phototransistors, photomultipliers, charge coupled devices or CMOS detectors. In various embodiments, the light detecting elements are selected and arranged in the sensing arm 1185 so as to be able read the assay status at each of the sensor pads 45.

In various embodiments, the light delivery arms 1183 are arranged so as to be fixed at an angle 45 degrees with respect to the normal to the surface of a fluidic chip 26 inside a cartridge 11 that has been inserted into the mechanical assembly 1182. Alternative configurations can be implemented using different angles. In these various embodiments, the amount of excitation light that may pass into the sensing arm 1185 is reduced. In other embodiments, two light delivery arms 1183 with a 90 degree angle between their optical axes may be employed to excite two parallel rows of sensor pads 45 within a fluidic chip 26. Alternative configurations can be implemented using different angles between the two light delivery arms 1183. In another embodiment, the sources of radiation 1184 are mounted into the light delivery arms 1183 using chip-on-board technology, an optical element is included in the delivery arm 1183 to collect, collimate and direct the light used to excite the fluorescent target-linker-label conjugates.

In various embodiments, fluorescent dyes are chosen with excitation wavelengths in the range of 620 nm to 650 nm, allowing inexpensive light emitting diodes can be used as the excitation sources 1184. These photophysical characteristics may lead to certain advantages for fluorescent immunoassays. Firstly, these excitation wavelengths are not absorbed by physiological fluids such as blood, serum, sweat, urine and: saliva. As a result, energy from the excitation source is not lost. Second, as the emission wavelength is Stokes shifted from the absorption wavelength, the fluorescence signal is not blocked by the optical filter 1187, Another possible advantage of this approach are the reduced background contributions to the fluorescence signal, due either to the materials employed for fabrication of the fluidic chip 26 or the sensor pads 45, the reagents that may be employed during the assays or other adventitious contaminants and impurities that may be present in oral fluid samples.

Figure 12:
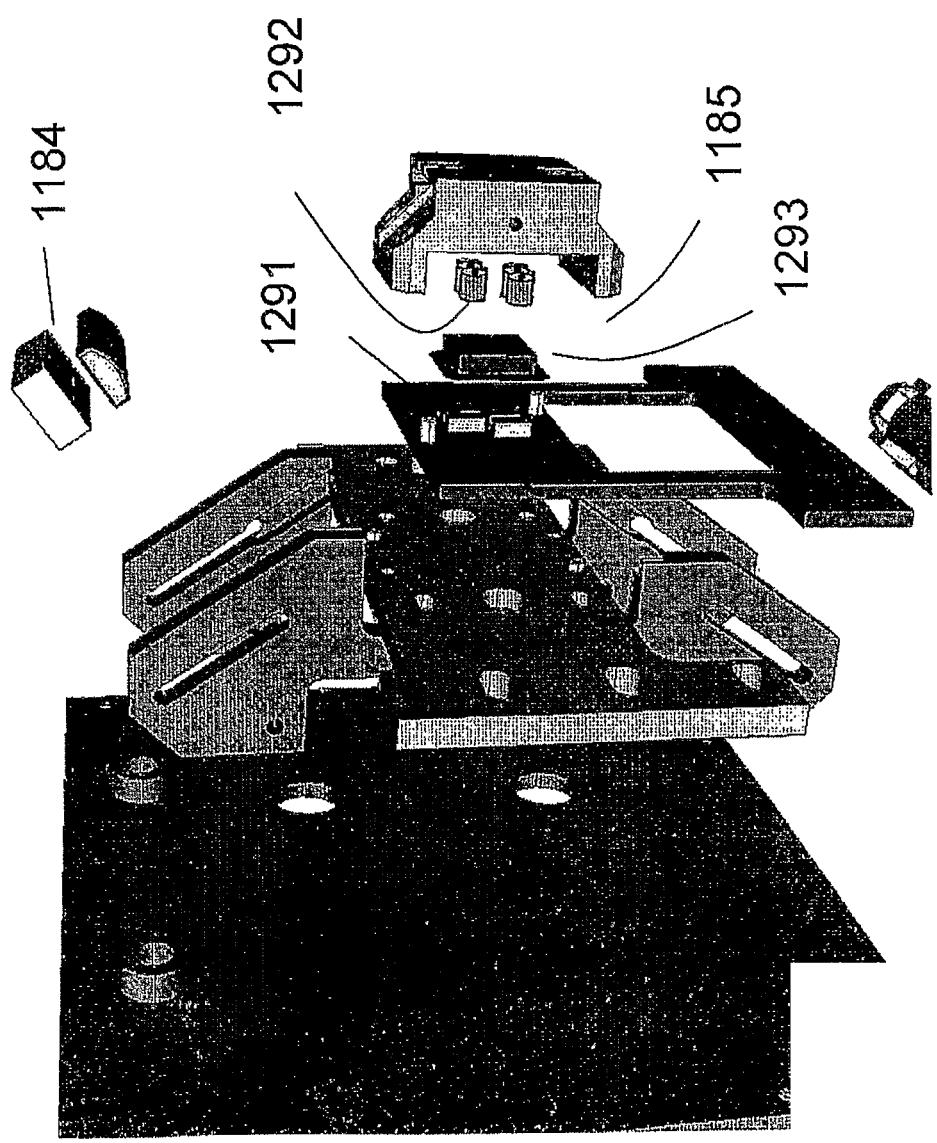
FIG. 12 shows a light detection arm of the module, and FIG. 13 features of the module that facilitate positioning and alignment of a cartridge.

Referring to FIG. 12, in various embodiments, to detect the fluorescence signals that arise following excitation of dyes in conjugates that have become bound at each of the sensor pads 45 during an assay, one photo integrated circuit 1291 is provided in the sensing arm 1185 for each sensor pad 45 in the fluidic chip 26. In various embodiments, this approach facilitates detection of the relevant fluorescence signals in parallel and, for example, no mechanical scanning of the sensor pads 45 across the sensing arm 1185 is required. The absence of moving parts in the reader 13 is an aid to maintaining optical alignment, increasing robustness and reducing manufacturing costs. In various embodiments, if a typical, commercially available light emitting diode is employed as the source of radiation 1184, and the label-linker-conjugates described previously are employed as the fluorescent reporter, the magnitude of the optical signal that may be detected at each sensor pad 45, under standard assay conditions for drugs of abuse with typical detection thresholds in the range of 10 to 100 ng/mL, can be greater than 100 pW of optical power. As a result, to collect and collimate the emitted fluorescence, an array of pinholes 1292 can be placed in the sensing arm 1185, in the optical path between the sensor pad 45 and the detecting element 1291, along with a filter 1187 to prevent any unwanted radiation from the light emitting diode 1184 reaching the detecting element 1291. Since pinholes are easier to align and less costly than lenses, this feature can further reduce manufacturing costs in various embodiments, while still providing the detection sensitivity necessary to carry out fluorescence-based assays for drugs of abuse. In another embodiment, fluorescence signal is collected by a light guide, for example a fibre-optic connection, and directed through the optical filter 1187 onto the detecting element 1291.

Figure 13:
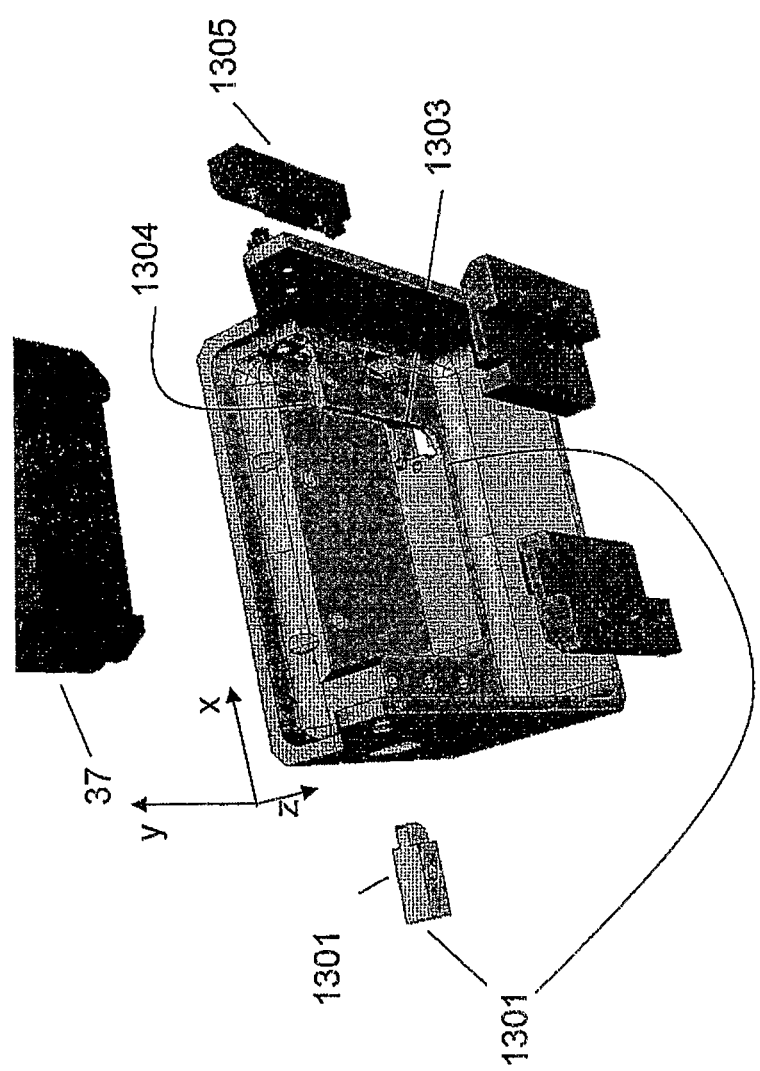

Referring to FIG. 13, a cartridge 11 may be equipped with guiding rails 37 that facilitate its insertion into the reader 13 and provide a first order of alignment between the reader 13 and the sensor pads 45 within the channels 42 of the fluidic chip 26. To provide more accurate alignment between the reader 13 and the sensor pads 45, the reader 13 may also be equipped with alignment parts 1301 which interact with features of the cartridge 11 by direct contact in order to ensure correct registration. In various embodiments, there is a chip location dowel 1302 which interacts with a feature 39/48 on the edge of the fluidic chip 26 within the cartridge 11 to ensure alignment of the chip with respect to the x direction. With commonly used methods of fabrication, an alignment tolerance of about 0.12 mm can be achieved. There is also a datum feature 1303 that interacts with the base of the chip to align it with respect to the y direction, again to a tolerance of 0.12 mm. Finally, there is a datum face 1304 against which the front 21 of the cartridge 11 is pressed to align it with respect to the z direction to a tolerance of about 0.1 mm. This approach thereby enables direct registration between the sensor pads 45 located within the channels 42 of the fluidic chip 26 and the optical elements within the reader 13. To ensure robust retention of registration, pressure may be applied to each of the alignment features by spring loaded bars 1305. As a result, in situations in which the analysis system 10 is used in non-laboratory environments, whereby it may be subjected to externally generated mechanical shocks, these tolerances are maintained in the event of a mechanical shock.

Figure 14:
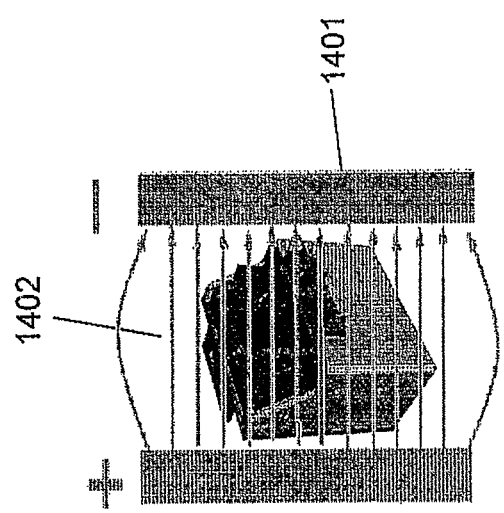
FIG. 14 is a diagram illustrating the optical detection reader in use in an electric field, not being affected by it.

Referring to FIG. 14, in various embodiments, the reader 13 is manufactured using external mechanical shielding 1401 in addition to electronic design practises that are known to confer resistance to environments containing high electric fields 1402. This enables the module 13 to operate in an error-free state in environments containing stray electric fields, or other high electric fields, such as those associated with professional mobile radio systems such as Terrestrial Trunked Radio (TETRA).

The invention is not limited to the embodiments described but may be varied in construction and detail in a manner that will be appreciated by those skilled in the art.

The invention claimed is:

1. A microfluidic structure comprising:
    a fluidic channel, configured to guide a flow of a fluid comprising a target analyte along a length of the fluidic channel in a first direction, the fluidic channel having a width in a second direction perpendicular to the first direction and a depth in a third direction perpendicular to the first direction and the second direction, the fluidic channel comprising a non-porous material;
    a reagent pad of porous material located within the fluidic channel and having a size in the second direction substantially similar to the width of the fluidic channel wherein the reagent pad has a size in the third direction that is substantially similar to the depth of the fluidic channel; and
    a sensor pad of porous material located within the fluidic channel and downstream from the reagent pad and having a size in the second direction substantially similar to the width of the fluidic channel, the reagent pad and the sensor pad being separated by a free space diffusion zone having a length in the first direction between 0.5 and 5 mm,
    wherein the sensor pad comprises immobilized target analyte-specific receptors that can bind the target analyte and/or a labelled product of a displacement, competition or sandwich affinity assay.

2. The microfluidic structure of claim 1, wherein the immobilized target analyte-specific receptors of the sensor pad can bind the target analyte and/or a labelled product of a displacement assay.

3. The microfluidic structure of claim 1, wherein the immobilized target analyte-specific receptors of the sensor pad can bind the target analyte and/or a labelled product of a competition assay.

4. The microfluidic structure of claim 3, wherein the reagent pad comprises releasable target analyte-linker-label conjugates and the immobilized target analyte-specific receptors of the sensor pad can bind the target analyte and/or the target analyte-linker-label conjugates.

5. The microfluidic structure of claim 1, wherein the immobilized target analyte-specific receptors of the sensor pad can bind the target analyte and/or a labelled product of a sandwich affinity assay.

6. The microfluidic structure of claim 1 further comprising a top layer that covers the fluidic channel.

7. The microfluidic structure of claim 6, wherein a portion of the top layer above the sensor pad comprises an optically clear inspection window allowing inspection of the sensor pad.

8. The microfluidic structure of claim 6, wherein there is a gap between the reagent pad or the sensor pad and the top layer.

9. The microfluidic structure of claim 8, wherein the gap is in the range of 0.05 to 0.5 mm.

10. The microfluidic structure of claim 6, wherein there is no gap between the reagent pad or the sensor pad and the top layer.

11. The microfluidic structure of claim 1 further comprising an absorption pad of fluid absorbing material located within the fluidic channel and downstream from the sensor pad.

12. The microfluidic structure of claim 11, wherein the sensor pad and the absorption pad are separated by a second diffusion zone.

13. The microfluidic structure of claim 1, wherein the pads are held in place via recesses which form part of the fluidic channel.

14. The microfluidic structure of claim 1, wherein the pads are held in place via a single or multiple discontinuous areas of adhesive coatings which form part of the fluidic channel.

15. The microfluidic structure of claim 1, wherein the pads are integrated into the fluidic channel as part of a supporting assembly of non-porous material.

16. The microfluidic structure of claim 15, wherein the pads are held in place via a single or multiple discontinuous areas of adhesive coatings which form part of the supporting assembly.

17. The microfluidic structure of claim 15, wherein the supporting assembly is held in place via a recess which forms part of the fluidic channel.

18. The microfluidic structure of claim 15, wherein the supporting assembly is held in place via a single or multiple discontinuous areas of adhesive coatings which form part of the fluidic channel.

19. The microfluidic structure of claim 15, wherein the supporting assembly is held in place via a single or multiple discontinuous areas of adhesive coatings on the underside of the supporting assembly.

20. The microfluidic structure of claim 1, wherein the fluidic channel has an opening at the downstream end of the channel to act as a vent to assist fluid flow in the first direction.

21. The microfluidic structure of claim 20, wherein the size of the opening of the vent is between about 0.1 and 5 mm.

22. The microfluidic structure of claim 1, wherein the length of the fluidic channel is between about 25 and 50 mm, the width of the fluidic channel is between about 1.3 and 5 mm and the depth of the fluidic channel is between about 0.25 and 1 mm.

23. The microfluidic structure of claim 1, wherein the cross-sectional area of the fluidic channel is between about 0.3 and 5 mm$^2$.

24. The microfluidic structure of claim 23, wherein the pads have widths of between about 1.3 and 5 mm and lengths of between about 2 and 25 mm.

25. The microfluidic structure of claim 1, wherein the labelled product of a displacement, competition or sandwich affinity assay includes a fluorescent label.

26. The microfluidic structure of claim 1, wherein the immobilized target analyte-specific receptors are antibodies that bind the target analyte and/or the labelled product of a displacement, competition or sandwich affinity assay.

27. The microfluidic structure of claim 1, wherein the immobilized target analyte-specific receptors are antigens that are bound by the target analyte and/or the labelled product of a displacement, competition or sandwich affinity assay.

28. The microfluidic structure of claim 1, wherein the immobilized target analyte-specific receptors are molecularly imprinted polymers that bind the target analyte and/or the labelled product of a displacement, competition or sandwich affinity assay.

29. A fluidic chip comprising a plurality of separate microfluidic structures as defined in claim 1.

30. The fluidic chip of claim 29, further comprising a single top layer that covers the fluidic channels of the plurality of microfluidic structures.

31. The fluidic chip of claim 29, wherein the plurality of separate microfluidic structures are spaced by between about 0.5 and 5 mm.

32. A sampling cartridge comprising an extraction chamber, a draining chamber, and the fluidic chip according to claim 29, wherein:
the extraction chamber is in fluid communication with the draining chamber via a draining duct, fluid travelling from the extraction chamber to the draining chamber in a first direction;
the draining chamber is configured to spread fluid from the extraction chamber in a second direction and in a third direction; and
each of the plurality of separate microfluidic structures comprising a fluidic channel in fluid communication with the draining chamber via a sample inlet port.

33. The sampling cartridge of claim 32, wherein:
the draining chamber includes:
i. a top reservoir and a bottom reservoir, fluid flowing from the top reservoir into the bottom reservoir in the first direction, the top and bottom reservoirs having widths in a second direction perpendicular to the first direction and depths in a third direction perpendicular to the first direction and the second direction;
ii. an interface between the top and bottom reservoirs in the form of an elongated slot extending in the second direction;
the fluidic chip includes a distribution chamber in communication with the bottom reservoir of the draining chamber, fluid travelling from the draining chamber to the distribution chamber in the first direction, the distribution chamber configured to spread fluid flow from the bottom reservoir in the second direction and in the third direction; and
the fluidic chip includes a plurality of separate microfluidic structures, each comprising a fluidic channel in fluid communication with the distribution chamber via a sample inlet port.

34. The sampling cartridge of claim 33, wherein the depth of the bottom reservoir of the draining chamber in the third direction is between about 0.25 and 2 mm.

35. The sampling cartridge of claim 33, wherein the depth of the bottom reservoir of the draining chamber in the third direction is substantially the same as a dimension of the distribution chamber of the fluidic chip.

36. The sampling cartridge of claim 33, wherein the width of the bottom reservoir of the draining chamber in the second direction is substantially the same as a dimension of the distribution chamber of the fluidic chip.

37. The sampling cartridge of claim 32 wherein the immobilized target analyte-specific receptors of the sensor pad can bind the target analyte and/or a labelled product of a displacement assay.

38. The sampling cartridge of claim 32, wherein the immobilized target analyte-specific receptors of the sensor pad can bind the target analyte and/or a labelled product of a competition assay.

39. The sampling cartridge of claim 38, wherein the reagent pad comprises releasable target analyte-linker-label conjugates and the immobilized target analyte-specific receptors of the sensor pad can bind the target analyte and/or the target analyte-linker-label conjugates.

40. The sampling cartridge of claim 32, wherein the immobilized target analyte-specific receptors of the sensor pad can bind the target analyte and/or a labelled product of a sandwich affinity assay.

41. The sampling cartridge of claim 32, wherein the draining chamber is configured to separate one or more bubbles from the fluid flowing through the draining chamber.

42. The sampling cartridge of claim 32, wherein the interface between the top and bottom reservoirs is configured to filter impurity particles from the fluid flowing through the draining chamber.

43. The sampling cartridge of claim 32, wherein the reagent pad and the sensor pad within each microfluidic structure are separated by a free space diffusion zone having a length in the first direction between 0.5 and 5 mm.

44. The sampling cartridge of claim 32, wherein each microfluidic structure comprises a fluidic channel having a width between about 1.3 and 5 mm and a depth between about 0.25 and 1 mm and a cross-sectional area of the fluidic channel is between about 0.3 and 5 mm$^2$.

45. The sampling cartridge of claim 32, further comprising an inspection window for inspecting the sensor pad in each microfluidic structure.

46. The sampling cartridge of claim 32, wherein the fluidic chip further comprises a single top layer that covers the fluidic channels of the plurality of separate microfluidic structures.

47. The sampling cartridge of claim 46, wherein there is no possibility of fluid cross-over between the plurality of separate microfluidic structures.

48. The sampling cartridge of claim 46, wherein the plurality of separate microfluidic structures are spaced by between about 0.5 and 5 mm.

49. The sampling cartridge of claim 32, wherein the fluidic chip is arranged in the sampling cartridge such that fluid flows along the fluidic channels of the microfluidic structures in the first direction.

50. The sampling cartridge of claim 32, wherein the fluidic chip is arranged in the sampling cartridge such that fluid flows along the fluidic channels of the microfluidic structures in the third direction.

51. The sampling cartridge of claim 32,
wherein the sampling cartridge comprises a swab pressing means.

52. The sampling cartridge of claim 51, wherein the pressing means comprises a hinged handle, wherein closure of the handle causes an inserted swab to be pressed and a fluid to flow from the swab into the extraction chamber.

53. The sampling cartridge of claim 32, wherein the sampling cartridge comprises a membrane over the extraction chamber to allow injection of a fluid by a syringe.

54. An analysis system comprising:
the sampling cartridge as defined in claim 32; and
an optical detection reader comprising a socket to receive at least part of the sampling cartridge, and an optical system for inspecting the sensor pad in each microfluidic structure through the inspection window of the sampling cartridge.

55. The analysis system of claim 54, wherein the sampling cartridge includes guiding rails that facilitate its insertion into the optical detection reader.

56. A method comprising flowing a fluid through the sampling cartridge of claim 49 wherein the first direction is in an upright direction.

* * * * *